US012668486B2

(12) United States Patent
Storms et al.

(10) Patent No.: US 12,668,486 B2
(45) Date of Patent: Jun. 30, 2026

(54) CONTAMINATED HYDROGEN GAS COMPOSITION AND ITS USE AS A REFERENCE FOR HYDROGEN FUELS

(71) Applicants: TOYOTA MOTOR EUROPE, Brussels (BE); NPL MANAGEMENT LIMITED, Teddington (GB)

(72) Inventors: Ward Storms, Brussels (BE); Thomas Bacquart, Teddington (GB); Abigail Morris, Teddington (GB)

(73) Assignees: TOYOTA JIDOSHA KABUSHIKI KAISHA, Toyota (JP); NPL MANAGEMENT LIMITED, Teddington (GB)

( * ) Notice: Subject to any disclaimer, the term of this patent is extended or adjusted under 35 U.S.C. 154(b) by 778 days.

(21) Appl. No.: 18/004,458

(22) PCT Filed: Jul. 8, 2020

(86) PCT No.: PCT/EP2020/069267
§ 371 (c)(1),
(2) Date: Jan. 6, 2023

(87) PCT Pub. No.: WO2022/008048
PCT Pub. Date: Jan. 13, 2022

(65) Prior Publication Data
US 2023/0249967 A1 Aug. 10, 2023

(51) Int. Cl.
*C01B 3/00* (2026.01)
*F17C 1/14* (2006.01)
(Continued)

(52) U.S. Cl.
CPC .................. *C01B 3/00* (2013.01); *F17C 1/14* (2013.01); *G01N 31/22* (2013.01);
(Continued)

(58) Field of Classification Search
None
See application file for complete search history.

(56) References Cited

U.S. PATENT DOCUMENTS 5,441,990 A * 8/1995 Robin ...................... C01B 3/48
518/703

FOREIGN PATENT DOCUMENTS

EP 1918247 A1 * 5/2008 .......... B01J 31/0225
WO 2019/156212 A1 8/2019

OTHER PUBLICATIONS

Frederique Haloua et al., "Metrology for hydrogen energy applications: a project to address normative requirements," Measurement Science and Technology, IOP, Bristol, GB, vol. 29, No. 3, Feb. 6, 2018 (Feb. 6, 2018), p. 34001, XP020324727, ISSN: 0957-0233, DOI: 10.1088/1361-6501/AA99AC.

(Continued)

*Primary Examiner* — John J Figueroa
(74) *Attorney, Agent, or Firm* — Dickinson Wright, PLLC

(57) ABSTRACT

The present invention relates to a hydrogen gas composition comprising specific gas contaminants at threshold limit values (as listed in the ISO 14687:2019 standard). The invention also concerns a metal cylinder such as an aluminium cylinder comprising a hydrogen gas composition according to the invention.

The hydrogen gas composition of the invention may be used as a calibration composition and/or quality control composition for controlling hydrogen fuels.

20 Claims, 8 Drawing Sheets

(51) Int. Cl.
| | |
|---|---|
| *G01N 31/22* | (2006.01) |
| *G01N 33/28* | (2006.01) |
| *H01M 8/04082* | (2016.01) |

(52) U.S. Cl.
CPC .... *G01N 33/2835* (2013.01); *H01M 8/04216* (2013.01); *C01P 2006/80* (2013.01); *F17C 2201/0104* (2013.01); *F17C 2203/0607* (2013.01); *F17C 2203/0643* (2013.01); *F17C 2203/0646* (2013.01); *F17C 2209/232* (2013.01); *F17C 2221/012* (2013.01); *F17C 2221/03* (2013.01); *F17C 2223/035* (2013.01); *F17C 2223/036* (2013.01)

(56) References Cited

OTHER PUBLICATIONS

Arrhenius K et al., "Development and evaluation of a novel analyser for ISO14687 hydrogen purity analysis," Measurement Science and Technology, IOP, Bristol, GB, vol. 31, No. 7, May 4, 2020 (May 4, 2020), p. 75010, XP020354412, ISSN: 0957-0233, DOI: 10.1088/1361-6501/AB7CF3.

Murugan Arul et al., "Measurement challenges for hydrogen vehicles," International Journal of Hydrogen Energy, Elsevier Science Publishers B.V., Barking, GB, vol. 44, No. 35, Jul. 19, 2019 (Jul. 19, 2019) , pp. 19326-19333, XP085731189, ISSN: 0360-3199, DOI: 10.1016/J.IJHYDENE.2019.03.190.

Bacquart Thomas et al., "Hydrogen fuel uality from two main production processes: Steam methane reforming and proton exchange membrane water electrolysis," Journal of Power Sources, Elsevier SA, CH, vol. 444, Oct. 22, 2019 (Oct. 22, 2019), XP085920783, ISSN: 0378-7753, DOI: 10.1016/J.JPOWSOUR.2019.227170.

* cited by examiner

Figure 15

CONTAMINATED HYDROGEN GAS COMPOSITION AND ITS USE AS A REFERENCE FOR HYDROGEN FUELS

RELATED APPLICATION

This application is a 371 of International Application No. PCT/EP2020/069267, filed on Jul. 8, 2020, including the specification, drawings and abstract, the entire disclosure of which is incorporated herein by reference.

FIELD OF THE INVENTION

The present invention relates to a contaminated hydrogen gas composition comprising specific gas contaminants, as well as to its use as a calibration composition and/or quality control composition for controlling hydrogen fuels. The invention also relates to a method for calibrating a hydrogen fuel device and/or carrying out quality control of a hydrogen fuel device.

Technological Background

According to European directive EN 17124, Hydrogen Refuelling Stations (HRSs) must comply with the ISO 14687:2019 standard (the revised version of the ISO14687-2:2012 standard), which describes the quality specification of hydrogen fuel for Fuel Cell Electrical Vehicles (FCEVs). It consists of a list of fourteen (14) gas contaminants and details threshold limits for each of these contaminants in hydrogen fuel. The contaminants detailed are based on known contaminants from current production methods for hydrogen and performance loss issues that can be associated with the presence of these contaminants.

Gas mixtures containing inert gases and high (relative to the ISO 14687:2019 standard) concentrations of $H_2S$ in hydrogen are available from companies like Air Liquide & Praxair. An example of an available gas mixture is nitrogen ($N_2$), carbon monoxide (CO), carbon dioxide ($CO_2$), argon (Ar), helium (He), methane ($CH_4$), water ($H_2O$), oxygen ($O_2$), and hydrogen suphide ($H_2S$) at 0.1 μmol/mol, in a hydrogen matrix.

The main problems related to current capability are that:

the available gas mixtures do not cover the entire range of impurities of the ISO 14687:2019 standard, and especially the reactive gases (i.e. formaldehyde, formic acid, ammonia, halogenated compounds), and the available concentrations of contaminants do not match the values stipulated in the ISO 14687:2019 standard.

Therefore, there is currently no commercial gas standard containing all the contaminants regulated in the ISO 14687:2019 standard which can be used as a calibration or quality control composition for controlling hydrogen fuel.

The present invention proposes a hydrogen gas composition comprising a set of gas contaminants (excluding either ammonia or formaldehyde) according to the ISO 14687:2019 standard, with appropriate stability, embodiments advantageously being capable of remaining stable for a minimum of 100 days (minimum of 50 days for formic acid). Such a hydrogen gas composition also leads to simplification and cost reduction of project management and dangerous goods shipments as, instead of managing a set of gases required to cover the entire ISO 14687:2019 group of gas contaminants (for example for international inter-laboratory testing comparisons), the shipment of one or two gas cylinders may be sufficient.

The hydrogen gas composition of the invention can be used as a calibration composition or quality control composition, for example for the following purposes:

to analyse hydrogen fuel according to the ISO 14687:2019 standard with a single gas sample, to test hydrogen fuel in fuel cells, to develop new techniques, equipment and devices, such as new hydrogen purifying devices like filters and hydrogen impurity sensors, in particular for fuel cell electric vehicles (FCEVs) or hydrogen refuelling stations (HRSs).

SUMMARY OF THE INVENTION

The present invention, in one aspect, relates to a hydrogen gas composition comprising a number of the gas contaminants listed in the ISO 14687:2019 standard (excluding either ammonia or formaldehyde). The work of the present inventors has sought, within the context of ranges of contaminant concentrations that can be appropriately used to calibrate analytic equipment for analysis in view of the ISO standard, to provide gas mixtures with appropriate stability.

In another aspect, the invention relates to a cylinder such as an aluminium cylinder comprising a hydrogen gas composition according to the invention.

A method for preparing a cylinder such as an aluminium cylinder according to the invention is also part of the invention.

The invention also relates to the use of a hydrogen gas composition according to the invention as a calibration composition and/or quality control composition. The concentration of the gas contaminants can be measured at the nozzle of a Hydrogen Refuelling Station (HRS), in application of the present invention, to be compared with the reference compositions of the present invention.

Finally, the invention also relates to a method for calibrating a hydrogen fuel device or carrying out quality control of a hydrogen fuel device.

BRIEF DESCRIPTION OF THE FIGURES

Figure 15:
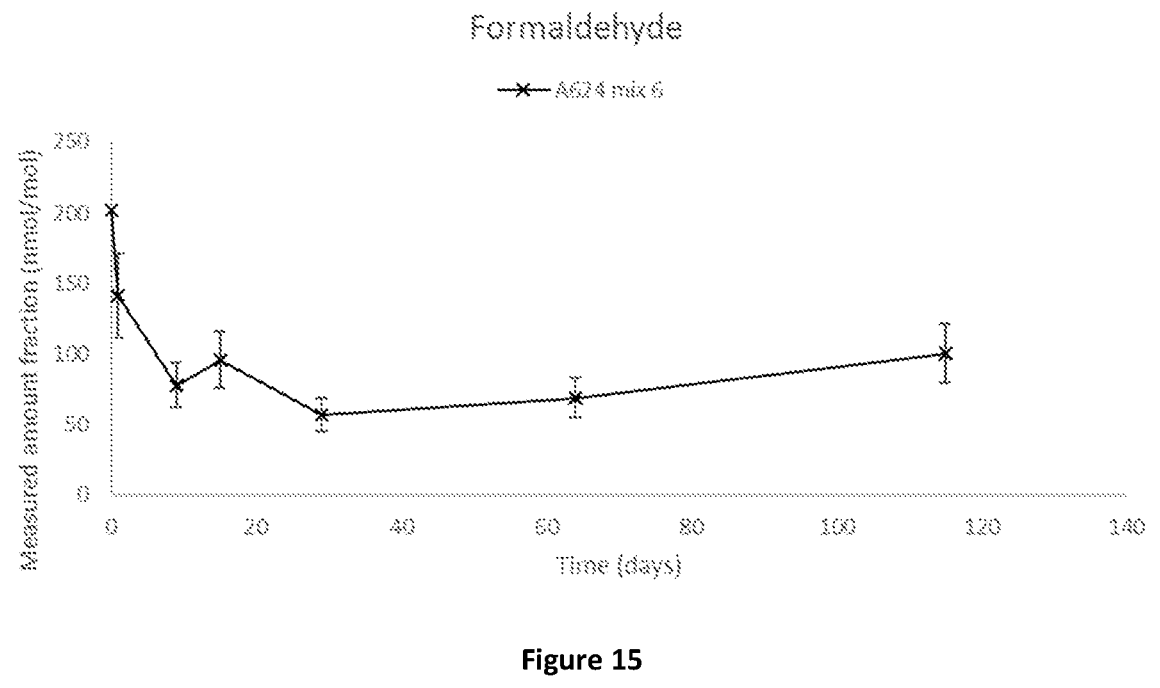

FIG. 15 shows the measured amount fraction of formaldehyde over time for the stability test samples. The value shown at age "0" days is the water gravimetric amount fraction calculated from the preparation for each cylinder.

DETAILED DESCRIPTION OF THE INVENTION

Figure 1:
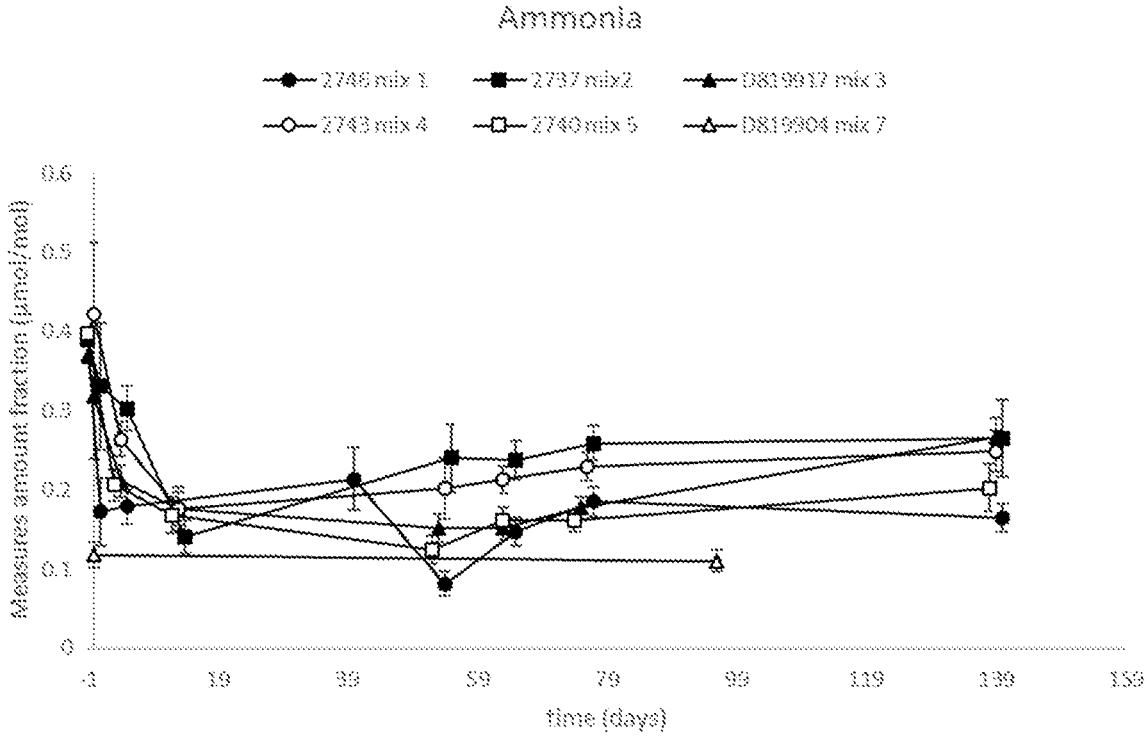
FIG. 1 shows the measured amount fraction of ammonia over time for the stability test samples. The value shown at age "−1" days is the ammonia gravimetric amount fraction calculated from the preparation for each cylinder.

The present invention relates to a hydrogen gas composition comprising the following gas contaminants in the following concentrations in a hydrogen gaseous matrix, expressed in μmol/mol with respect to the total number of moles of gas in the hydrogen gas composition as a whole:
   sulphur compound(s): at least 0.002 μmol/mol and at most 0.20 μmol/mol,
   formaldehyde (HCHO): at least 0.05 μmol/mol at most 0.50 μmol/mol,
   formic acid (HCOOH): at least 0.05 μmol/mol and at most 0.50 μmol/mol),
   ammonia (NH$_3$): at least 0.050 μmol/mol and at most 0.50 μmol/mol,
   halogenated compound(s): at least 0.020 μmol/mol and at most 0.20 μmol/mol),
the hydrogen gas composition comprising either ammonia (NH$_3$) or formaldehyde (HCHO) but not ammonia and formaldehyde simultaneously. This first group of contaminants can be considered as group (1) in terms of the relative importance of their analytical tracking.

In preferred embodiments, the hydrogen gas composition additionally comprises the following further gas contaminants at the following concentrations in the hydrogen gaseous matrix, expressed in μmol/mol with respect to the moles of gas in the hydrogen gas composition as a whole:
   water (H$_2$O): at least 2.0 μmol/mol and at most 10 μmol/mol),
   oxygen (O$_2$): at least 2.0 μmol/mol and at most 10 μmol/mol.

This second group of contaminants (water and oxygen) can be considered as group (2) in terms of the relative importance of their analytical tracking.

In preferred embodiments, the hydrogen gas composition additionally comprises, preferably in addition to water and oxygen as given above, the following further gas contaminants at the following concentrations in the hydrogen gaseous matrix, expressed in μmol/mol with respect to the moles of gas in the hydrogen gas composition as a whole:
   hydrocarbon(s) except methane: at least 0.20 μmol/mol and at most 5 μmol/mol),
   methane (CH$_4$): at least 0.20 μmol/mol and at most 150 μmol/mol,
   helium (He): at least 150 μmol/mol and at most 2500 μmol/mol,
   nitrogen (N$_2$): at least 50 μmol/mol and at most 450 μmol/mol,
   argon (Ar): at least 50 μmol/mol and at most 450 μmol/mol,
   carbon dioxide (CO$_2$): at least 0.50 μmol/mol and at most 5.0 μmol/mol,
   carbon monoxide (CO): at least 0.10 μmol/mol and at most 0.5 μmol/mol.

This third group of contaminants can be considered as group (3) in terms of the relative importance of their analytical tracking.

In preferred hydrogen gas compositions of the invention, the hydrogen gaseous matrix represents at least 99.97 mol % of the total hydrogen gas mixture. In preferred hydrogen gas compositions of the invention, the non-hydrogen gas concentration is less than or equal to 300 μmol/mol.

Therefore, according to an embodiment, the hydrogen gas composition of the invention comprises ammonia (NH$_3$) but no formaldehyde (CH$_2$O). According to another embodiment, the hydrogen gas composition of the invention comprises formaldehyde (CH$_2$O) but no ammonia (NH$_3$).

The hydrogen gaseous matrix of the hydrogen gas composition of the invention advantageously represents at least 99.97 mol % of the total hydrogen-based gas mixture.

In the hydrogen gas composition of the invention, the non-hydrogen gases concentration may thus preferably represent less than or equal to 300 μmol/mol of the total hydrogen-based gas mixture.

According to a preferred embodiment, the hydrocarbon(s) (other than methane) present in the hydrogen gas composition of the invention contain(s) ethane (C$_2$H$_6$) and may consist of ethane. In appropriate embodiments, ethane is thus used as the most simple non-methane hydrocarbon. However, other hydrocarbons like propane, butane etc. may be used for calibration or quality control purposes—the ISO 14687:2019 specification only stipulates "total hydrocarbons" in this respect and thus other hydrocarbons can be used. In practice, hydrocarbons of not more than 5 carbon atoms, including branched hydrocarbons may be used, such as pentane, isobutane and isopentane.

According to another preferred embodiment, the sulphur compound(s) present in the hydrogen gas composition of the invention contain(s) hydrogen sulphide (H$_2$S) or carbonyl sulphide (OCS). The ISO 14687:2019 specification only stipulates "total sulphur" in this respect. Hydrogen sulphide (H$_2$S) is highly relevant as it is the most likely sulphur component which could be present at the Hydrogen Refuelling Stations (HRSs), although it may react with other species including at surfaces. Other sulphur species like mercaptans may also be used. The hydrogen gas-based mixture of the invention may comprise both $H_2S$ and OCS.

According to another preferred embodiment, the halogenated compound(s) present in the hydrogen gas-based composition of the invention contain(s) dichloromethane $(CH_2Cl_2)$ and may consist of this species. The ISO 14687: 2019 specification only stipulates "total halogenated compounds" in this respect. Apart from dichloromethane, other small organohalogen compounds may be used, for example molecules with four carbon atoms or less, preferably only one or two carbon atoms, and with four halogen atoms or less, preferably only one or two halogen atoms.

Hydrogen gas compositions of the invention may have the advantage of showing a guaranteed stability over a period of time of at least 50 days, and preferably 100 days. In preferred embodiments, all the contaminant gas species except formic acid (HCOOH) may show high stability for a period of 100 days, with formic acid (HCOOH) showing a lifetime of 50 days.

In another aspect, the invention is directed to a metal cylinder, preferably an aluminium cylinder, or a stainless steel cylinder, comprising a hydrogen gas composition according to present invention under a pressure ranging from at least 20 to at most 200 bars.

The metal cylinder, preferably an aluminium cylinder or a stainless steel cylinder, used to contain a hydrogen gas composition according to present invention, may be polished or coated. A silicon-based coating may be used to create a uniform film of silicon-based compounds on the aluminium substrate, using for example silicon dioxide or $Si_3N_4$, trimethylsilane or dimethylsilane gas applied by chemical vapor deposition or sputtering. This kind of deposition may be applied for example by using the techniques of EP patent 0 165 413 B1, or U.S. Pat. No. 5,047,131. Such a silicon-based coating may for example be a commercially available Spectra-seal® coating. Such a silicon-based coating is preferably not used in the presence of hydrogen sulphide $(H_2S)$, but can appropriately be used in the presence of carbonyl sulphide (COS).

According to a preferred embodiment, the inner surface of the aluminium cylinder used in the invention may also be one prepared by a fine-polishing process, the cylinder being subject to a final polishing step to create a freshly exposed aluminium surface, for example by the use of a wet grinding procedure in the presence of a surfactant. The surfactant may appropriately be derived from C6-C18 carboxylic acids as described for example in EP 2 195 141. Such surface-polished aluminium cylinders are available commercially, for example as Luxfer SGS® finish products. Such surface-polished aluminium cylinders are appropriately used when hydrogen sulphide $(H_2S)$ is present, and/or halogenated compound(s), in the hydrogen gas-based mixture.

In another aspect, the invention also provides a kit comprising:

one aluminium cylinder comprising a hydrogen gas composition according to the present invention and comprising ammonia (but not formaldehyde), and
one aluminium cylinder comprising a hydrogen gas composition according to the present invention and comprising formaldehyde (but not ammonia).

The kit of the invention is of particular interest since ammonia and formaldehyde cannot be present together in the same hydrogen gas composition because of spontaneous and immediate reaction between these two contaminants to form a by-product (i.e. hexamine). Therefore, a set of two cylinders (one containing ammonia, and the other one containing formaldehyde) is required in order to achieve the full range of gas contaminants listed in the ISO 14687:2019 standard.

It may also be envisaged to have two separate kits, each of them having an ammonia- (and not formaldehyde-) containing cylinder and a formaldehyde- (and not ammonia-) containing cylinder, where one of the two kits contains two metal cylinders, such as an aluminium cylinders, with a silicon-based coating, and contains carbonyl sulphide as sulphur species, and the other kit contains two metal cylinders, such as an aluminium cylinders, not having such a silicon-based coating but instead surface-polished aluminum cylinders, the hydrogen gas compositions containing contaminants of the latter two cylinders containing hydrogen sulphide.

In another aspect, the invention relates to a method for preparing a cylinder, such as an aluminium cylinder comprising the steps of:

(i) optionally pre-treating the inner surface of a metal cylinder, preferably an aluminium cylinder, by pre-saturating the inside of the cylinder, preferably an aluminium cylinder, with ammonia $(NH_3)$ and/or with a sulphur species, preferably hydrogen sulphide $(H_2S)$;

(ii) introduction, in the metal, preferably aluminium, cylinder obtained at the end of step (i) of the contaminants of group (1) set out above, ammonia $(NH_3)$ not being introduced when formaldehyde (HCHO) is present and vice versa, versa, and with formaldehyde (HCHO) preferably introduced before formic acid (HCOOH), with preferably also introduction of the contaminants of group (2) and/or group (3) set out above.

The pre-treatment procedure (i) is useful in order to render the $H_2S$ and $NH_3$ adsorption sites on the inner cylinder surface inert, by adsorbing on them before the actual gas mixture will be introduced (after flushing and vacuuming). The $H_2S$ and $NH_3$ of the actual mixture will stay in the gas phase as the adsorption sites are already occupied with the $H_2S$ and $NH_3$ from the pre-saturation procedure. In view of the incompatibility of ammonia and formaldehyde, pre-treatment with ammonia $(NH_3)$ should not be performed when HCOH is intended to be in the gas mixture, as HCOH will react with the pre-adsorbed $NH_3$ on the cylinder wall, resulting in loss of stability. Pre-treatment with ammonia $(NH_3)$ is advantageous when $NH_3$ (and not formaldehyde) is intended to be contained in the mixture. Pre-treatment with hydrogen sulphide $(H_2S)$ is similarly appropriate in particular when it is intended to include hydrogen sulphide $(H_2S)$ as sulphur contaminant.

According to an advantageous process strategy, after optional surface pre-treatment (i) and addition of contaminants (ii), the hydrogen of the matrix is the last gas added.

The aluminium cylinder pre-treated during step (i) may be coated with a surface-polish finish or treated by passivation by deposition of silicon-based compounds.

During the pre-treatment step (i), the pre-saturation is advantageously maintained during at least 48 hours with ammonia $(NH_3)$ and hydrogen sulphide $(H_2S)$ concentrations higher than 10 µmol/mol, when the aluminium cylinder is treated by passivation, preferably by deposition of silicon-based compounds as is known commercially for example as the SPECTRA-SEAL® coating treatment.

During step (ii), the introduction of the gas contaminants in the metal, preferably aluminium cylinder is advantageously carried out according to a gravimetrical method wherein each gas contaminant is transferred separately from a cylinder containing a higher concentration of one gas contaminant to the aluminium cylinder obtained at the end of step (i) which is positioned on a balance allowing the measurement of the exact quantity of the added gas contaminant, with formaldehyde (HCHO) introduced before formic acid (HCOOH). According to a preferred embodiment, formaldehyde (HCHO), formic acid (HCOOH) and ammonia ($NH_3$) are introduced during step (ii) in a concentration which is 50% higher than their maximum individual concentration in the final hydrogen gas composition according to the present invention. This overdosing helps to compensate the losses occurring during the preparation of the hydrogen gas composition.

During step (ii), the gas contaminants may be introduced one by one into the metal cylinder, such as an aluminium cylinder or stainless steel cylinder. According to a preferred embodiment, the following inert gas contaminants: nitrogen ($N_2$), helium (He), argon (Ar), carbon monoxide (CO), carbon dioxide ($CO_2$), methane ($CH_4$), and ethane ($C_2H_6$), in their maximum individual concentrations, are introduced in this order into the cylinder in the form of a pre-blended mixture during step (ii). Instead of ethane, hydrocarbons in the form of C2-C5 linear and branched hydrocarbons are possible, although it is preferred to use ethane.

This pre-blended mixture is preferably prepared according to a gravimetrical method as defined above wherein each inert gas contaminant is transferred separately from a cylinder containing a higher concentration of one gas contaminant to another cylinder which is positioned on a balance allowing the measurement of the exact quantity of the added inert gas contaminant.

In another aspect, the invention also relates to the use of a hydrogen gas composition according to the present invention as a calibration and/or quality control composition, and in particular:

as a calibration composition and/or quality control composition to analyse hydrogen fuel according to the ISO14687:2019 standard, as a calibration composition and/or quality control composition to test hydrogen fuel in fuel cells, as a calibration composition and/or quality control composition for manufacturing hydrogen purifying devices such as those working by pressure swing adsorption or temperature adsorption, and preferably for calibration and/or quality control of filters and hydrogen impurity sensors, in particular for fuel cell electric vehicles (FCEVs) or hydrogen refuelling stations (HRSs).

Finally, the invention relates to a method for calibrating and/or carrying out quality control composition of a hydrogen fuel device, and preferably a fuel cell electric vehicle (FCEV) or a hydrogen refuelling station (HRS), using the hydrogen gas composition, metal cylinder or kit of the invention.

Any combination of the above described elements in all possible variations thereof is encompassed by the invention unless otherwise indicated herein or otherwise clearly contradicted by context. Thus, all features and embodiments described herein in particular as applicable, advantageous or preferred in the context of the invention are to be construed as being applicable in combination with one another, in preferred embodiments of the invention.

EXAMPLES

The following examples assessed the stability performed on different hydrogen gas compositions comprising contaminants over a 4 month period.

1—Preparation of Gas Contaminant Mixtures

The following gas contaminants mixtures were prepared:

Composition 1 was prepared to contain the full list of gas contaminants according to the invention at amount fractions close to their threshold levels. Target amount fractions of ammonia ($NH_3$), formaldehyde (HCHO), hydrogen sulphide ($H_2S$) and formic acid (HCOOH) were increased to compensate losses during the gas transfer. Composition 1 was prepared in an aluminium cylinder treated internally with a silicon compound-based coating (SPECTRA-SEAL® available from BOC, UK) (from hereinafter referred to as "Mix 1") and in an aluminium cylinder with surface polishing (Luxfer SGS® internal finish) (from hereinafter referred to as "Mix 3").

Composition 2 (from hereinafter referred to as "Mix 2") was prepared to contain the full list of gas contaminants according to the invention at amount fractions close to their threshold levels but excluding formaldehyde (HCHO) and formic acid (HCOOH) to try and reduce possible reactions between these acidic compounds and the ammonia ($NH_3$) and hydrogen sulphide ($H_2S$) present in the sample.

Composition 3 (from hereinafter referred to as "Mix 4") was prepared to contain the full list of gas contaminants according to the invention at amount fractions close to their threshold levels but excluding formic acid (HCOOH) to investigate if removal of this compound would allow the hydrogen sulphide ($H_2S$) to remain stable within the mixture.

Composition 4 (from hereinafter referred to as "Mix 5") was prepared to contain the full list of gas contaminants according to the invention at amount fractions close to their threshold levels. In this composition the hydrogen sulphide ($H_2S$) was replaced with carbonyl sulphide (OCS) to investigate the possibility of using alternative sulphur compounds as a calibrant and/or quality control component.

Composition 5 was prepared to contain the full list of gas contaminants according to the invention at amount fractions close to their threshold levels without increase in targeting to compensate for preparation losses. Composition was prepared in an aluminum cylinder treated internally with a silicon compound-based coating (SPECTRA-SEAL® available from BOC, UK) (from hereinafter referred to as "Mix 6").

Composition 6 was prepared to contain the full list of gas contaminants according to the invention at amount fractions close to their threshold levels to mimic "Mix 3" but with reduced $H_2S$ target to achieve a level that was even closer to the threshold levels. Composition 6 was prepared in an aluminium cylinder with surface polishing (Luxfer SGS® internal finish) (from hereinafter referred to as "Mix 7").

The compositions of the different gas contaminant mixtures are resumed in Table 1 below in terms of target values:

TABLE 1

Targeted values for gas contaminant mixtures

| | Amount fraction (in µmol/mol) | | | | | | |
|---|---|---|---|---|---|---|---|
| Contaminants | "Mix 1" | "Mix 2" | "Mix 3" | "Mix 4" | "Mix 5" | "Mix 6" | "Mix 7" |
| Carbon monoxide (CO) | 0.2 | 0.2 | 0.2 | 0.2 | 0.2 | 0.2 | 0.2 |
| Carbon dioxide ($CO_2$) | 2 | 2 | 2 | 2 | 2 | 2 | 2.15 |
| Methane ($CH_4$) | 1 | 1 | 1 | 1 | 1 | 1 | 1 |
| Ethane ($C_2H_6$) | 0.5 | 0.5 | 0.5 | 0.5 | 0.5 | 0.5 | 0.5 |
| Nitrogen ($N_2$) | 100 | 100 | 100 | 100 | 100 | 100 | 100 |
| Argon (Ar) | 100 | 100 | 100 | 100 | 100 | 100 | 100 |
| Helium (He) | 1200 | 1200 | 1200 | 1200 | 1200 | 1200 | 1500 |
| Ammonia ($NH_3$) | 0.1-0.3 | 0.1-0.3 | 0.1-0.3 | 0.1-0.3 | 0.1-0.3 | 0.1-0.3 | 0.4 |
| Formic acid (HCOOH) | 0.2-0.3 | — | 0.2-0.3 | — | 0.2-0.3 | 0.2-0.3 | 0.4 |
| Formaldehyde (HCHO) | 0.2-0.3 | — | 0.2-0.3 | 0.2-0.3 | 0.2-0.3 | 0.2-0.3 | 0.4 |
| Hydrogen sulphide ($H_2S$) | 0.005-0.015 | 0.005-0.015 | 0.005-0.015 | 0.005-0.015 | — | 0.005-0.015 | 0.004-0.007 |
| Dichloromethane ($CH_2Cl_2$) | 0.05 | 0.05 | 0.05 | 0.05 | 0.05 | 0.05 | 0.05 |
| Water ($H_2O$) | 5 | 5 | 5 | 5 | 5 | 5 | 5 |
| Oxygen ($O_2$) | 5 | 5 | 5 | 5 | 5 | 5 | 5 |
| Carbonyl sulphide (OCS) | — | — | — | — | 0.005-0.015 | — | — |

2—Materials and Preparation Methods

2.1—Cylinders

The samples "Mix 1", "Mix 2", "Mix 4" and "Mix 5" were prepared in 10 L aluminium cylinders (Luxfer, UK) with an internal silicon compound-based coating (SPECTRA-SEAL® coating, BOC, UK). The cylinders were fitted with BS341 No. 15 valve outlets (Rotarex, LU). The cylinders for samples "Mix 1", "Mix 2", "Mix 4" and "Mix 5" underwent a hydrogen sulphide pre-treatment process involving an exposure to >10 µmol/mol $H_2S$ over 3 days. The cylinders then underwent an ammonia ($NH_3$) pre-treatment which consists in transferring a small mass of high amount fraction PRM of ammonia ($NH_3$) in hydrogen (>20 µmol/mol ammonia) and homogenizing the cylinders by rolling for a minimum of two hours. The cylinders were then left for a minimum of 48 hours to condition before being evacuated on a turbomolecular pump for a minimum of 12 hours.

The sample "Mix 3" was prepared in a 10 L aluminium cylinder (Luxfer, UK) with internal surface-polishing (SGS®) finish and fitted with DIN 477 No. 1 valve outlet (Rotarex, LU). The cylinder to be used for sample "Mix 3" was evacuated for a minimum of 12 hours using a turbomolecular vacuum pump.

2.2—Materials

Samples "Mix 1", "Mix 2", "Mix 4" and "Mix 5" were prepared by diluting the contaminants listed in Table 2 below in the indicated amounts in hydrogen of high purity >99.9999%, Hydrogen BIP® Plus (Air Products, UK).

TABLE 2

List of materials and contaminant amount fractions

| Contaminants | Amount fraction (µmol/mol) |
|---|---|
| Helium (He) | 2935 ± 24 |
| Argon (Ar) | 1022.1 ± 3.6 |
| Nitrogen ($N_2$) | 1034.0 ± 4.2 |
| Carbon monoxide (CO) | 1.999 ± 0.012 |
| Carbon dioxide ($CO_2$) | 19.9 ± 0.07 |
| Methane ($CH_4$) | 9.891 ± 0.041 |
| Ethane ($C_2H_6$) | 4.759 ± 0.021 |
| Helium (He) | 3000 ± 25 |

TABLE 2-continued

List of materials and contaminant amount fractions

| Contaminants | Amount fraction (µmol/mol) |
|---|---|
| Argon (Ar) | 1024.9 ± 3.6 |
| Nitrogen ($N_2$) | 993.5 ± 4.2 |
| Carbon monoxide (CO) | 2.003 ± 0.012 |
| Carbon dioxide ($CO_2$) | 21.28 ± 0.07 |
| Methane ($CH_4$) | 10.693 ± 0.043 |
| Ethane ($C_2H_6$) | 5.231 ± 0.022 |
| Ammonia ($NH_3$) | 2.005 ± 0.023 |
| Ammonia ($NH_3$) | 22.47 ± 0.24 |
| Dichloromethane ($CH_2Cl_2$) | 0.991 ± 0.008 |
| Oxygen ($O_2$) | 50.57 ± 0.19 |
| Water ($H_2O$) | 50.35 ± 0.18 |
| Water ($H_2O$) | 49.77 ± 0.10 |
| Carbonyl sulphide (OCS) | 0.2003 ± 0.0047 |
| Hydrogen sulphide ($H_2S$) | 0.2012 ± 0.0013 |
| Formaldehyde (HCHO) | 3.81 ± 0.20 |

2.3—Preparation

The samples were prepared gravimetrically by gas transfer. A high pressure cylinder was connected to a lower pressure cylinder via a gas transfer line. The pressure difference allowed gas transfer from the higher pressure into the low pressure cylinders in which the samples were prepared. The lower pressure cylinder was placed on a balance that was used to monitor the mass of gas transferred. A calculated mass of gas was then transferred from the higher pressure cylinder into the lower pressure cylinder.

The cylinder used to prepare each sample was weighed against a tare on a top pan electronic balance of type XPE26003LC (Mettler Toledo, US). The sample cylinders were weighed once they had been evacuated, before gas addition and again after each addition. The mass of the contaminants transferred was calculated using the mass difference between the cylinder before and after the gas transfer.

The gas transfer line used was a ¹⁄₁₆" Sulfinert© (Thames Restek, UK) treated tubing with Swagelok® connections with a minimum-dead-volume (MDV) connection at each end to connect to the cylinder. The transfer the line was leaked checked using an electronic leak detection device (Thames Restek, UK).

For each gas transfer, the transfer line was purged to remove air from the line. This was done by a pressurizing and depressurizing cycle. This purging process was repeated at each cylinder valve a minimum of 4 times.

After the additions were complete the sample cylinders were rolled for a minimum of two hours to homogenize the gas mixture.

Table 3a below shows the addition order of each contaminant in the different gas contaminant mixtures.

TABLE 3a

| Amount fraction (in µmol/mol) | | | | | | |
|---|---|---|---|---|---|---|
| "Mix 1" | "Mix 2" | "Mix 3" | "Mix 4" | "Mix 5" | "Mix 6" | "Mix 7" |
| Day 1 | | | | | | |
| Dichloromethane (CH₂Cl₂) (NG813) | Dichloromethane (CH₂Cl₂) (NG813) | Ammonia (NH₃) (2108R) | Ammonia (NH₃) (2108R) | Dichloromethane (CH₂Cl₂) (NG813) Day 2 | Dichloromethane (CH₂Cl₂) (NG813) | Oxygen (O₂) (2056R3) |
| Water (H₂O) (NG591R2) | Water (H₂O) (NG591R2) | Dichloromethane (CH₂Cl₂) (NG813) | Dichloromethane (CH₂Cl₂) (NG813) | Ammonia (NH3) (NG717R2) | Formic acid (HCOOH) (2381R) | Formic acid (HCOOH) (2381R2) |
| Permanent gases (1901R2) | Permanent gases (1901R2) | Formaldehyde (HCHO) (2042R2) | Formaldehyde (HCHO) (2042R2) Day 2 | Formaldehyde (HCHO) (2042R2) | Oxygen (O₂) (1530R3) | Formaldehyde (HCHO) (L5303044_R) |
| Oxygen (O₂) (2056R3) | Oxygen (O₂) (2056R3) | Permanent gases (1901R2) Day 2 | Permanent gases (1901R2) | Oxygen (O₂) (2056R3) | Water (H₂O) (A498R) | Water (H₂O) (A498R2) |
| Ammonia (NH₃) (NG717R2) | Ammonia (NH₃) (NG717R2) | Water (H₂O) (NG591R2) | Water (H₂O) (NG591R2) | Formic acid (HCOOH) (2381R2) | Permanent gases (1901R) Day 2 | Dichloromethane (CH₂Cl₂) (1918R3) |
| Formaldehyde (HCHO) (2042R2) | Hydrogen sulphide (H₂S) (NG692R2) Day 2 | Oxygen (O₂) (2056R3) | Oxygen (O₂) (2056R3) | Permanent gases (1823R3) | Ammonia (NH₃) (NG717R) | Ammonia (NH₃) (NG717R3) |
| Formic acid (HCOOH) (2381R2) Day 2 | Hydrogen BIP ® Plus | Hydrogen sulphide (H₂S) (NG692R2) | Hydrogen sulphide (H₂S) (NG692R2) | Water (H₂O) (A498R2) | Formaldehyde (HCHO) (2056R2) | Permanent gases (1823R3) |
| Hydrogen sulphide (H₂S) (NG692R2) | | Formic acid (HCOOH) (2381R2) | Hydrogen BIP ® Plus | Carbonyl sulphide (OCS) (2085R2) Day 3 | Hydrogen Sulphide (H₂S) (NG807) | Hydrogen sulphide (H₂S) (NG692R2) |
| Hydrogen BIP ® Plus | | Hydrogen BIP ® Plus | | Hydrogen BIP ® Plus | Hydrogen BIP ® Plus | Hydrogen BIP ® Plus |

* Permanent gases is a mixture of helium (He), Argon (Ar), Nitrogen (N₂), carbon monoxide (CO), carbon dioxide (CO₂), methane (CH₄) and ethane (C₂H₆) (1901R2 or 1823R3)

Table 3b below shows the amount fractions during preparation of each contaminant in the different gas contaminant mixtures.

TABLE 3b

| Contaminants | Amount fraction (in µmol/mol) | | | | | | |
|---|---|---|---|---|---|---|---|
| | "Mix 1" | "Mix 2" | "Mix 3" | "Mix 4" | "Mix 5" | "Mix 6" | "Mix 7" |
| Carbon monoxide (CO) | 0.197 | 0.194 | 0.197 | 0.198 | 0.195 | 0.194 | 0.198 |
| Carbon dioxide (CO₂) | 1.960 | 1.935 | 1.964 | 1.970 | 2.072 | 1.930 | 2.110 |
| Methane (CH₄) | 0.974 | 0.962 | 0.976 | 0.979 | 1.039 | 0.959 | 1.058 |
| Ethane (C₂H₆) | 0.468 | 0.462 | 0.469 | 0.471 | 0.508 | 0.461 | 0.518 |
| Nitrogen (N₂) | 102 | 101 | 102 | 102 | 97 | 100 | 98 |
| Argon (Ar) | 101 | 99 | 101 | 101 | 100 | 99 | 101 |
| Helium (He) | 1541 | 1539 | 1505 | 1524 | 1508 | 1537 | 1536 |
| Ammonia (NH₃) | 0.398 | 0.389 | 0.369 | 0.395 | 0.398 | 0.196 | 0.404 |
| Formic acid (HCOOH) | 0.213 | — | 0.205 | — | 0.211 | 0.225 | 0.393 |
| Formaldehyde (HCHO) | 0.267 | — | 0.258 | 0.265 | 0.269 | 0.202 | 0.312 |
| Hydrogen sulphide (H₂S) | 0.015 | 0.016 | 0.015 | 0.015 | — | 0.0067 | 0.0061 |

TABLE 3b-continued

| | Amount fraction (in μmol/mol) | | | | | | |
|---|---|---|---|---|---|---|---|
| Contaminants | "Mix 1" | "Mix 2" | "Mix 3" | "Mix 4" | "Mix 5" | "Mix 6" | "Mix 7" |
| Dichloromethane (CH₂Cl₂) | 0.051 | 0.049 | 0.049 | 0.052 | 0.049 | 0.047 | 0.052 |
| Water (H₂O) | 4.98 | 5.02 | 5.06 | 5.03 | 4.99 | 5.02 | 5.02 |
| Oxygen (O₂) | 5.07 | 5.08 | 4.92 | 5.00 | 4.93 | 5.08 | 5.02 |
| Carbonyl sulphide (OCS) | — | — | — | — | 0.015 | — | — |

3—Analytical Methods 3.1—Calibration 3.1.1—Comparative Method Using a PRIM

Amount fractions in mixtures can be quantified using PRMs (Primary Reference Materials). The amount fraction in the PRM should be within 10% of the amount fraction of the mixture being quantified to reduce effects of possible non-linearity of detectors. If the linearity of the detector has been proven over the range of interest, then a PRM of amount fraction that is not within 10% of the amount fraction of the mixture being quantified can be used and an additional uncertainty consideration applied.

The amount fraction of the mixture of interest is quantified by using the response factor (RF) of the validated PRM. The RF is a measure of the instrument response compared to the amount fraction being analyzed. This is calculated via the equation:

$$RF_{PRM} = \frac{R_{PRM}}{A_{PRM}} \qquad \text{(equation 1)}$$

where:

$RF_{PRM}$ is the response factor of the PRM being analyzed.
$R_{PRM}$ is the instrument response of the PRM being analyzed.
$A_{PRM}$ is the validated amount fraction of the PRM being analyzed.

The amount fraction of the mixture of interest can then be quantified using the equation:

$$A_s = \frac{R_s}{RF_{PRM}} \qquad \text{(equation 2)}$$

where:

$A_s$ is the calculated measured amount fraction of the sample being analyzed.
$R_s$ is the instrument response of the sample being analyzed.
$RF_{PRM}$ is the response factor of the PRM being used to quantify the sample.

The relative expanded analytical uncertainty can then be calculated via the equation:

$$U = 2 \times \sqrt{\mu_{m,PRM}^2 + \mu_{m,s}^2 + \mu_{Grav}^2} \qquad \text{equation 3}$$

where:

U: is expanded uncertainty with k=2
$\mu_m$, is the uncertainty of measurements of the PRM in % (relative standard deviation [RSD])
$\mu_{m,s}$ is the uncertainty of sample (mixture being quantified) measurements in % (RSD)
$\mu_{Grav}$ is the uncertainty in the gravimetric value of the PRM amount fraction of the component of interest in %.

3.1.2—Dynamic Standard Calibrations

Where the contaminant of interest is known to be unstable at low amount fractions in high pressure cylinders a dynamic system was used to prepare the Reference Material (RM) instead. The dynamic system uses a high concentration PRM at an amount fraction that is known to be more stable and uses a diluent gas (in this case Hydrogen BIP® Plus) to generate a RM with the desired low amount fraction.

The dynamic systems used for generating low amount fraction RMs for this stability test used two mass flow controllers (MFCs) (Bronkhorst, NL). One MFC was used to control the flow of the diluent gas and one MFC was used to control the flow of the PRM. The PRM MFC was Sulfinert© treated to prevent loss of the reactive contaminant in the PRM being diluted inside the dynamic system.

The dilution ratios used varied between ⅟₅₀₀ to ⅟₅₀ for the single point dynamic RMs and the calibration curves produced in this test.

The different types of calibration that were done using a dynamic system in the stability test are described below.

3.1.2.1—Comparative Single Point Dynamic RM

In this case the dynamic system is to generate one dynamic RM close to the sample amount fraction (within 10%) which is used to quantify the amount fraction in the mixture of interest. As with use of a PRM, the RF of the generated RM amount fraction is used to quantify the amount fraction in the mixture of interest.

The RF and amount fraction of the mixture of interest are calculated using equations 1 and 2 respectively, the same as when using a PRM. The uncertainty is calculated via the equation:

$$U = 2 \times \mu_{m,PRM}^2 + \mu_{m,s}^2 + \mu_{MFC}^2 \qquad \text{(equation 4)}$$

where:

U: is expanded uncertainty with k=2
μm, is the uncertainty of measurements of the PRM in % (relative standard deviation [RSD])
$\mu_{m,s}$ is the uncertainty of sample (mixture being quantified) measurements in % (RSD)
$\mu_{MFC}$ is the uncertainty of the flows of the MFC system in % as this is the largest contribution to the uncertainty.

3.1.2.2—Calibration Using a Dynamically Generated Curve

In this case the dynamic system is used to generate several dynamic RMs of different amount fractions. The range of amount fractions generated with the dynamic system should cover f 50% of the sample amount fraction unless the sample amount fraction is below the limit of quantification.

Validated software XLGenline version 2 (NPL, UK) was used to quantify the measured amount fraction in the stability test mixtures. This software uses the RM amount fractions and the response of the instrument for both the RMs and the mixtures being quantified along with their associated uncertainties. The software generates a calibration curve which can then be used to quantify the amount fractions in the mixtures of interest. The software also generates an uncertainty.

3.1.2.3—Calibration Using a Curve of PRMs

In this case PRMs were used to generate a calibration curve. The range of amount fractions of the PRMs used should cover f 50% of the sample amount fraction unless the sample amount fraction is below the limit of quantification.

Validated software XLGenline version 2 (NPL, UK) was used to quantify the measured amount fraction in the stability test mixtures. This software uses the PRM amount fractions and the response of the instrument for both the PRMs and the mixtures being quantified along with their associated uncertainties.

The software generates a calibration curve which can then be used to quantify the amount fractions in the mixtures of interest. The software also generates an uncertainty.

3.1.3—Gravimetric RM Solutions

The thermal desorption gas chromatographer (TD-GC, Marks International, UK)) coupled with mass spectrometry and flame ionisation detector (MS-FID, Agilent Technologies, UK) described in section 3.2.5 uses RMs in liquid form for calibration. This relies on the ability of sorbent to trap contaminants (e.g. organo-halogenates) either from a gas mixture or from solutions in a similar way.

The RM solutions are produced gravimetrically by diluting the purity analysed contaminant of interest in a suitable solvent. Successive dilutions of these starting mixtures are then produced until a suitable range of amount fractions of RM with the contaminant of interest are available to produce a calibration curve.

These liquid standards can then be transferred onto the sorbent using a syringe that has been calibrated using mass measurements of solvent. The syringe is fitted with a Chaney adaptor to ensure the repeatability of the volume of the liquid standard injected.

According to previous international comparisons the method used produces the NPL gravimetric RM solutions with an uncertainty of less than 5%. The RSD of the RM solutions is considered to be less than 5%. A final expanded uncertainty of 20% was, therefore, provided as a conservative estimate.

3.2—Instrument Methods 3.2.1—Ammonia ($NH_3$)

Ammonia was measured using selected ion flow tube coupled with mass spectrometry (SIFT-MS), Voice 200 Ultra (Anatune, UK). The reagent used was $O_2^+$ and the reaction product $NH_3^+$ was measured and quantified by the instrument.

The ammonia amount fraction in the mixtures was quantified with the calibration using a dynamically generated curve method described in section 3.1.2.2.

For "Mix 6" ammonia was measured using fourier transform infra-red spectroscopy (FTIR). The instrument was a Nicolet 6700 (Thermo Fisher Scientific, UK) equipped with nitrogen purged multi-range optics, a KBr beam splitter and a liquid nitrogen cooled MCT-A detector. The spectrometer was fitted with a heated "White" type gas cell (Cyclone C5, Specac, UK), nominal path length: 8 m and volume=2 L, equipped with a borosilicate glass body and KBr windows. The gas cell conditions were typically T=30° C. and p=1055 mbar with a sample flow rate of 0.7-1 standard litre per minute (SLM). Single beam spectra were collected between 4000-0 cm-1 with a resolution set to 1 cm$^{-1}$ and each recorded spectrum consisted of an average of 180 individual spectra. The spectral range used to quantify the amount fraction of ammonia was between 975-956 cm$^{-1}$. The ammonia amount fraction when using FTIR was quantified using the comparative single point dynamic RM method described in section 3.1.2.1.

3.2.2—Argon (Ar)

Argon was measured using gas chromatography (GC) (Agilent Technologies, UK) coupled with a thermal conductivity detector (TCD) (Agilent Technologies, UK). The method used one HP-PLOT Q PT 15 m×0.53 mm×40 μm, one HP-PLOT Molsieve 30 m×0.53 mm×50 μm and a section of Fused Silica Tubing 0.25 mm cut to 1.5 m with helium carrier. The loop size used for sample injection was 2 mL.

The argon in the mixtures was quantified using the comparative method using a PRM described in section 3.1.1.

3.2.3—Carbon Dioxide ($CO_2$)

Carbon dioxide was measured using GC (Peak Laboratories, US) coupled with a methaniser and flame ionisation detector (FID). The method used a HaySep D column (186"×1.5") with nitrogen carrier with the column held at a temperature of 65 degrees Celsius. The loop size used for sample injection was 5 mL.

Carbon dioxide at time 181 days for "Mix 1" and "Mix2", 180 days for "Mix 3" and "Mix 4" and 179 days for "Mix 5" and 77 days for "Mix 6" was measured using GC-PDHID (Agilent Technologies, UK) (VICI, CH). The method used Packed column: HS-A, 100 μm×120 μm×2 m, 0.75 mm ID, 1/16" OD, silico NOC with helium carrier gas. The loop size used for sample injection was 1 mL.

The carbon dioxide amount fraction in the mixtures was quantified using the comparative method using a PRM described in section 3.1.1.

3.2.4—Carbon Monoxide (CO)

Carbon monoxide was measured using GC (Peak Laboratories, US) coupled with a methaniser FID. The method used a HaySep D column (186"×1.5") with nitrogen carrier with the column held at a temperature of 65° C. The loop size used for sample injection was 5 mL.

The carbon monoxide amount fraction in the mixtures was quantified with the comparative method using a PRM described in section 3.1.1.

3.2.5—Carbonyl Sulphide (OCS)

Carbonyl sulphide was measured using GC (Agilent Technologies, UK) coupled with a sulphur chemiluminescence detector (SCD) (Agilent Technologies, UK). The method used a HP-1 column (60 m×0.530 mm) with helium carrier. The sample loop size used for injection was 0.5 mL.

The hydrogen sulphide amount fraction in the mixtures was quantified with the calibration using a dynamically generated curve method described in section 3.1.2.2.

3.2.6—Dichloromethane ($CH_2Cl_2$)

Ammonia was measured using SIFT-MS, Voice 200 Ultra (Anatune, UK). The reagent used was $O_2^+$ and the reaction products $CH_2(^{35}Cl^-)(^{37}Cl^-)^+$ were used for response calculations for the instrument using a branching ratio of 56:38. The $CH_2(^{37}Cl^-)_2^+$ ion, with a branching ratio of 6, was not considered for the quantification.

The dichloromethane amount fraction in the mixtures was quantified with the calibration using a dynamically generated curve method described in section 3.1.2.2. The dichloromethane for "Mix 6" was analysed using a TD-GC (Markes International, UK) coupled with mass spectroscopy (MS) with a split FID (Agilent Technologies, UK). This system desorbs the analytes from the sorbent and releases the analytes onto a U-T6SUL cold trap. A DB-VRX column 60 m×0.25 mm with a helium carrier was used for separation. The dichloromethane amount fraction when measured by TD-GC-MS was quantified using the gravimetric RM solution method described in section 3.1.3.

3.2.7—Ethane ($C_2H_6$)

Ethane was measured using GC (Peak Laboratories, US) coupled with a methaniser FID. The method used a HaySep D column (186"×1.5") with nitrogen carrier with the column held at a temperature of 65° C. The loop size used for sample injection was 5 mL.

The ethane amount fraction in the mixtures was quantified with the comparative method using a PRM described in section 3.1.1.

3.2.8—Formaldehyde (HCHO)

Formaldehyde was measured using SIFT-MS, Voice 200 Ultra (Anatune, UK). The reagent used was $H_3O^+$ and reaction product $CH_3O^+$ was measured and quantified by the instrument.

At time 27 days for "Mix 1", time 22 days for "Mix 3", time 26 days for "Mix 4", time 21 days for "Mix 5" and time 25 days and all measurements for "Mix 6", formaldehyde was measured using GC (Peak Laboratories, US) coupled with a methaniser FID. The method used a Haysep D column (186"×1.5") with nitrogen carrier with the column held at a temperature of 170° C. The loop size used for sample injection was 10 mL.

The formaldehyde amount fraction in the mixtures was quantified using the calibration using a dynamically generated curve method described in section 3.1.2.2.

3.2.9—Formic Acid (HCOOH)

The formic acid was measured using SIFT-MS, Voice 200 Ultra (Anatune, UK). The reagent used was $H_3O^+$. The reaction products $HCOOH_2^+$ was measured and quantified by the instrument.

At time 15 days for "Mix 1" and time 13 days for "Mix 5" and all measurements for "Mix 6", formic acid was measured using FTIR. The instrument was a Nicolet 6700 (Thermo Fisher Scientific, UK) equipped with nitrogen purged multi-range optics, a KBr beam splitter and a liquid nitrogen cooled MCT-A detector. The spectrometer was fitted with a heated "White" type gas cell (Cyclone C5, Specac, UK), nominal path length: 8 m and volume=2 L, equipped with a borosilicate glass body and KBr windows.

The gas cell conditions were typically T=30° C. and p=1055 mbar with a sample flow rate of 0.7-1 standard litre per minute (SLM).

Single beam spectra were collected between 4000-0 cm$^{-1}$ with a resolution set to 1 cm$^{-1}$ and each recorded spectrum consisted of an average of 180 individual spectra.

The spectral range used to quantify the amount fraction of formic acid was between 1166-1062 cm$^{-1}$.

The formic acid amount fraction measurement instances $M_0$ and $M_7$ for all samples using the SIFT-MS were quantified with the comparative method using a PRM described in section 3.1.1.

The formic acid amount fraction in the mixtures when measured on the SIFT-MS was quantified with the calibration using a dynamically generated curve method described in section 3.1.2.2.

The formic acid amount fraction in the mixtures when measured using FTIR was quantified with the comparative method using a PRM described in section 3.1.1.

3.2.10—Helium (He)

Helium was measured using GC-TCD (Agilent Technologies, UK). The method used one HeyeSep Q 80/100 mesh 2 m×⅛" outer diameter×2.0 mm inner diameter column and one Molesieve 5A 80/100 mesh 9 ft×⅛" outer diameter×2 mm inner diameter column with hydrogen carrier. The loop size used for sample injection was 2 mL.

The helium amount fraction in the mixtures was quantified with the comparative method using a PRM described in section 3.1.1.

3.2.11—Hydrogen Sulphide ($H_2S$)

Hydrogen sulphide was measured using GC (Agilent Technologies, UK) coupled with an SCD (Agilent Technologies, UK). The method used a HP-1 column (60 m×0.530 mm) with helium carrier. The sample loop size used for injection was 0.5 mL.

The hydrogen sulphide amount fraction in the mixtures was quantified with the calibration using a dynamically generated curve method described in section 3.1.2.2.

3.2.12—Nitrogen ($N_2$)

Nitrogen was measured using GC-TCD (Agilent Technologies, UK). The method used one HP-PLOT Q PT 15 m×0.53 mm×40 μm, one HP-PLOT Molsieve 30 m×0.53 mm×50 μm and a section of Fused Silica Tubing 0.25 mm cut to 1.5 m with helium carrier. The loop size used for sample injection was 2 mL.

The nitrogen amount fraction in the mixtures was quantified the comparative method using a PRM described in section 3.1.1.

3.2.13—Methane ($CH_4$)

Methane at measurement instance $M_0$ for all samples was measured GC (Peak Laboratories, US) coupled with a methaniser FID. The method used a HaySep D column (186"×1.5") with nitrogen carrier with the column held at a temperature of 65° C. The loop size used for sample injection was 5 mL.

Methane at measurement instance M120 for "Mixes 1 to 5" was measured using GC-PDHID (Agilent Technologies, UK) (VICI, CH). The method used one Molesieve 5A capillary column, 30 m×0.53 mm×0.50 μm with helium carrier gas. The loop size used for sample injection was 1 mL.

The methane amount fraction in the mixtures was quantified with the comparative method using a PRM described in section 3.1.1.

3.2.14—Oxygen ($O_2$)

Oxygen was measured using GC-PDHID (Agilent Technologies, UK) (VICI, CH). The method used two Molesieve 5A capillary columns, one 30 m×0.53 mm×0.50 μm and one 50 m×0.53 mm×0.50 μm with helium carrier gas. The loop size used for sample injection was 1 mL.

The oxygen amount fraction in the mixtures was quantified with the calibration using a dynamically generated curve method described in section 3.1.2.2.

3.2.15—Water ($H_2O$)

Water was measured using quartz crystal microbalance, QMA401 (Michell, US).

Gases are sampled directly from the gas cylinder to the analyzer, a valve was used to restrict the pressure to 1 bar gauge into the QMA (flow to 0.333 $LH_2$/min) for the QMA. The gas line was extensively purged with high purity nitrogen (a BIP® high purity product with a nitrogen amount of at least 99.9999%, Air Products, UK) prior to analysis in order to remove any moisture from the tubing.

The water amount fraction in the mixtures was quantified using the calibration using the curve made from PRMs method described in section 3.1.3

4—Stability Test Results

The following Table 4a shows the concentrations for contaminants for Mixes 1 to 7 observed after 1 week.

TABLE 4a

| | Measured values after 1 week | | | | | | |
| | Amount fraction (in μmol/mol) | | | | | | |
| Contaminants | "Mix 1" | "Mix 2" | "Mix 3" | "Mix 4" | "Mix 5" | "Mix 6" | "Mix 7" |
|---|---|---|---|---|---|---|---|
| Carbon monoxide (CO) | 0.177 | 0.188 | 0.184 | 0.194 | 0.190 | 0.194 | 0.202 |
| Carbon dioxide (CO$_2$) | 2.12 | 2.00 | 2.12 | 2.07 | 1.83 | 1.95 | 2.140 |
| Methane (CH$_4$) | 0.979 | 0.976 | 0.989 | 1.004 | 1.08 | 0.964 | 1.061 |
| Ethane (C$_2$H$_6$) | 0.467 | 0.455 | 0.471 | 0.478 | 0.517 | 0.467 | 0.522 |
| Nitrogen (N$_2$) | 104 | 99 | 103 | 99 | 93 | 104 | 107 |
| Argon (Ar) | 106 | 103 | 106 | 104 | 102 | 106 | 111 |
| Helium (He) | 1680 | 1680 | 1630 | 1660 | 1650 | 1718 | 1540 |
| Ammonia (NH$_3$) | 0.179 | 0.303 | 0.211 | 0.264 | 0.168 | — | 0.118 |
| Formic acid (HCOOH) | 0.168 | — | 0.072 | — | 0.056 | 0.282 | 0.087 |
| Formaldehyde (HCHO) | — | — | — | — | — | 0.096 | — |
| Hydrogen sulphide (H$_2$S) | — | — | 0.0145 | — | — | — | 0.006 |
| Dichloromethane (CH$_2$Cl$_2$) | 0.062 | 0.056 | 0.056 | 0.061 | 0.058 | 0.049 | 0.052 |
| Water (H$_2$O) | 5.8 | 5.9 | 5.4 | 5.4 | 5.3 | 5.7 | 5.5 |
| Oxygen (O$_2$) | 5.04 | 4.57 | 4.71 | 4.65 | 4.76 | 4.72 | 4.85 |
| Carbonyl sulphide (OCS) | — | — | — | — | 0.0149 | — | — |

4.1—Ammonia (NH$_3$)

All samples showed an initial loss of ammonia amount fraction over the first few days of measurement. The samples retained detectable ammonia at a level close to half the target amount fraction for the remainder of the stability test.

Due to that initial loss seen in the preparation of ammonia at ISO14687 threshold levels, standard fuels prepared containing ammonia at threshold amount fractions would have to use a measured certified amount fraction.

An estimation of the stability from day 15 to the end of the test showed that the ammonia amount fractions were within 10% relative variation (see FIG. 1).

"Mix 6" showed initial loss to below limit of detection of ammonia.

4.2—Argon (Ar)

Figure 2:
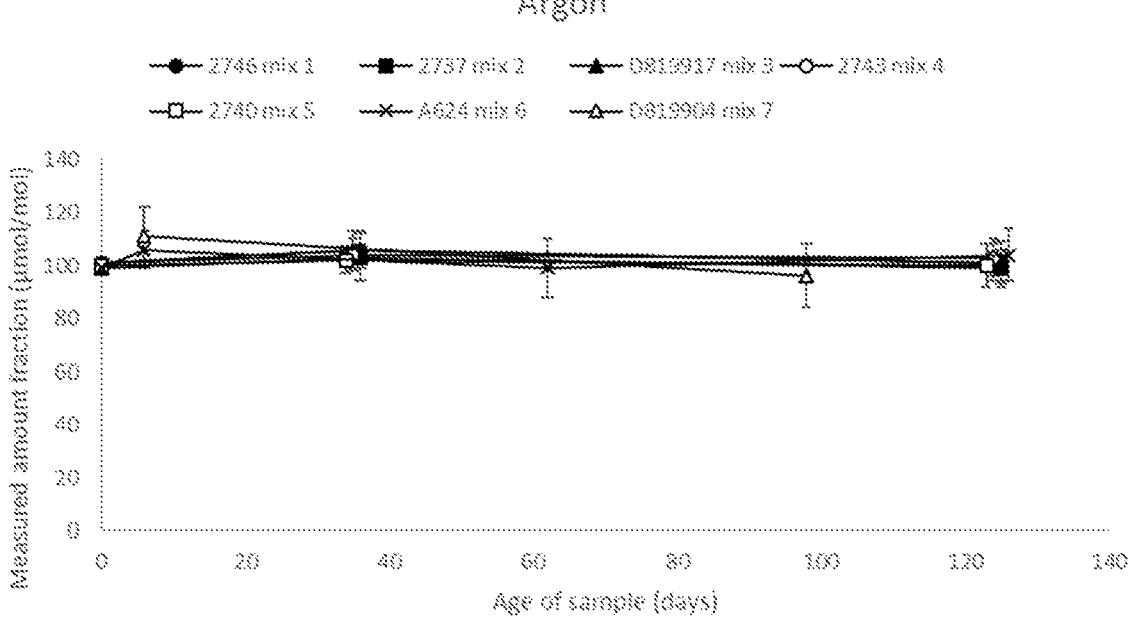
FIG. 2 shows the measured amount fraction of argon over time for the stability test samples. The value shown at age "0" days is the argon gravimetric amount fraction calculated from the preparation for each cylinder.

The amount fraction of argon in samples "Mix 1", "Mix 2", "Mix 3", "Mix 4", "Mix 5", "Mix 6" and "Mix 7" showed no initial loss within a 95% confidence level. The amount fraction of argon in these samples remained stable at a 95% confidence level for the duration of the stability test (124 days for "Mixes 1-5", 126 days for "Mix 6" and 98 days for "Mix 7"). This can be seen in FIG. 2.

4.3—Carbon Dioxide (CO$_2$)

Figure 3:
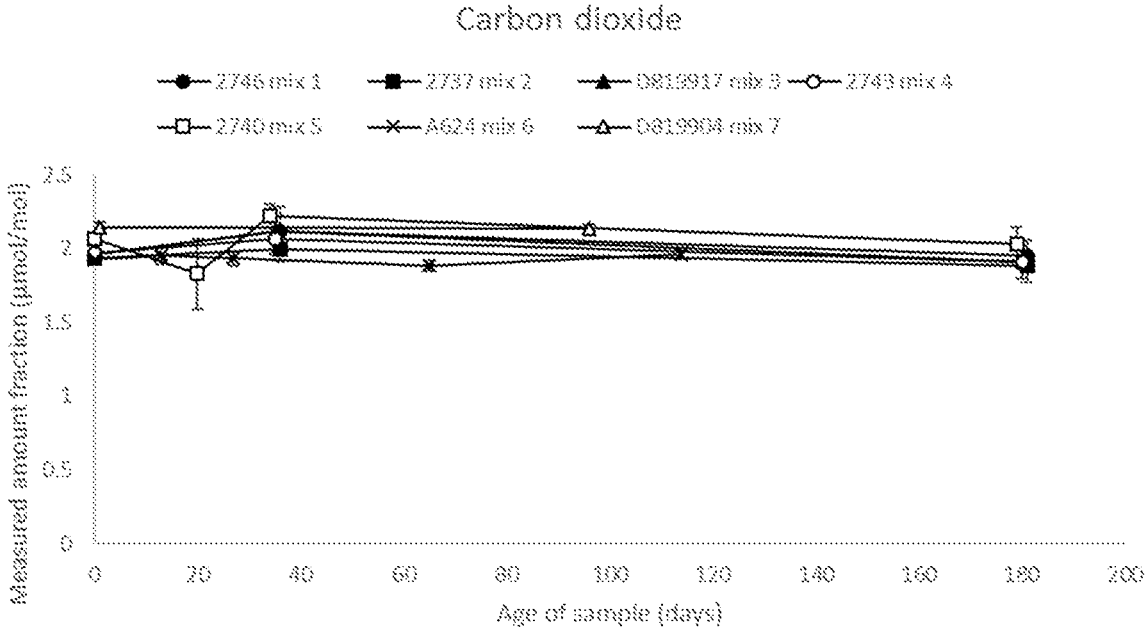
FIG. 3 shows the measured amount fraction of carbon dioxide over time for the stability test samples. The value shown at age "0" days is the carbon dioxide gravimetric amount fraction calculated from the preparation for each cylinder.

The amount fraction of carbon dioxide in samples "Mix 1", "Mix 2", "Mix 3", "Mix 4", "Mix 5", "Mix 6" and "Mix 7" showed no initial loss within a 95% confidence level. The amount fraction of carbon dioxide in these samples remained stable at a 95% confidence level for the duration of the stability test (180 days for "Mixes 1-5", 114 days for "Mix 6" and 96 days for "Mix 7"). This can be seen in FIG. 3.

4.4—Carbon Monoxide (CO)

Figure 4:
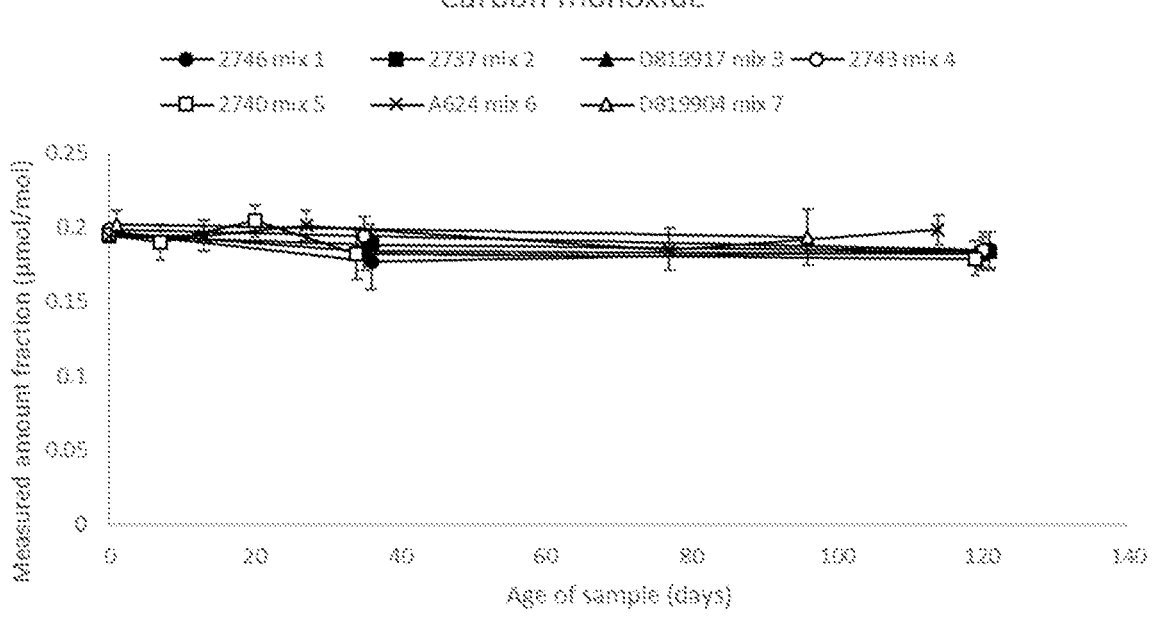
FIG. 4 shows the measured amount fraction of carbon monoxide over time for the stability test samples. The value shown at age "0" days is the carbon monoxide gravimetric amount fraction calculated from the preparation for each cylinder.

The amount fraction of carbon monoxide in samples "Mix 1", "Mix 2", "Mix 3", "Mix 4", "Mix 5", "Mix 6" and "Mix 7" showed no initial loss within a 95% confidence level. The amount fraction of carbon dioxide in these samples remained stable at a 95% confidence level for the duration of the stability test (180 days for "Mixes 1-5", 114 days for "Mix 6" and 96 days for "Mix 7"). This can be seen in FIG. 4.

4.5—Carbonyl Sulphide (OCS)

Figure 5:
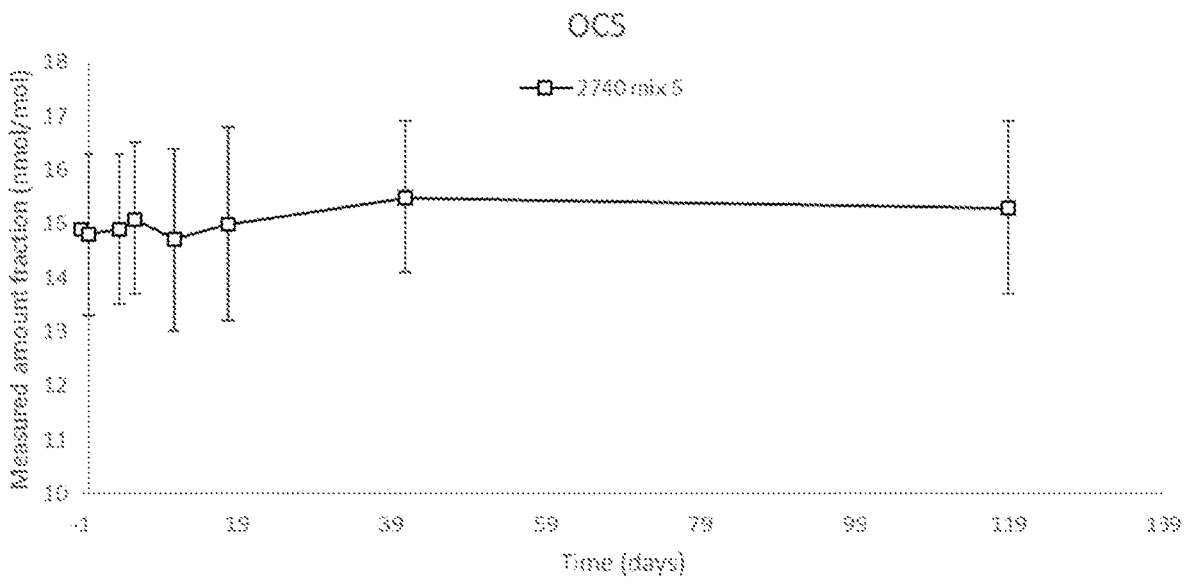
FIG. 5 shows the measured amount fraction of carbonyl sulphide over time for the stability test sample "Mix 5". The value shown at age "−1" days is the carbonyl sulphide gravimetric amount fraction calculated from the preparation for the cylinder "Mix 5".

The amount fraction of carbonyl sulphide in the sample "Mix 5" showed no initial loss within a 95% confidence level. The amount fraction of carbonyl sulphide in this sample remained stable at a 95% confidence level for the duration of the stability test (119 days). This can be seen in FIG. 5.

4.6—Dichloromethane (CH$_2$Cl$_2$)

Figure 6:
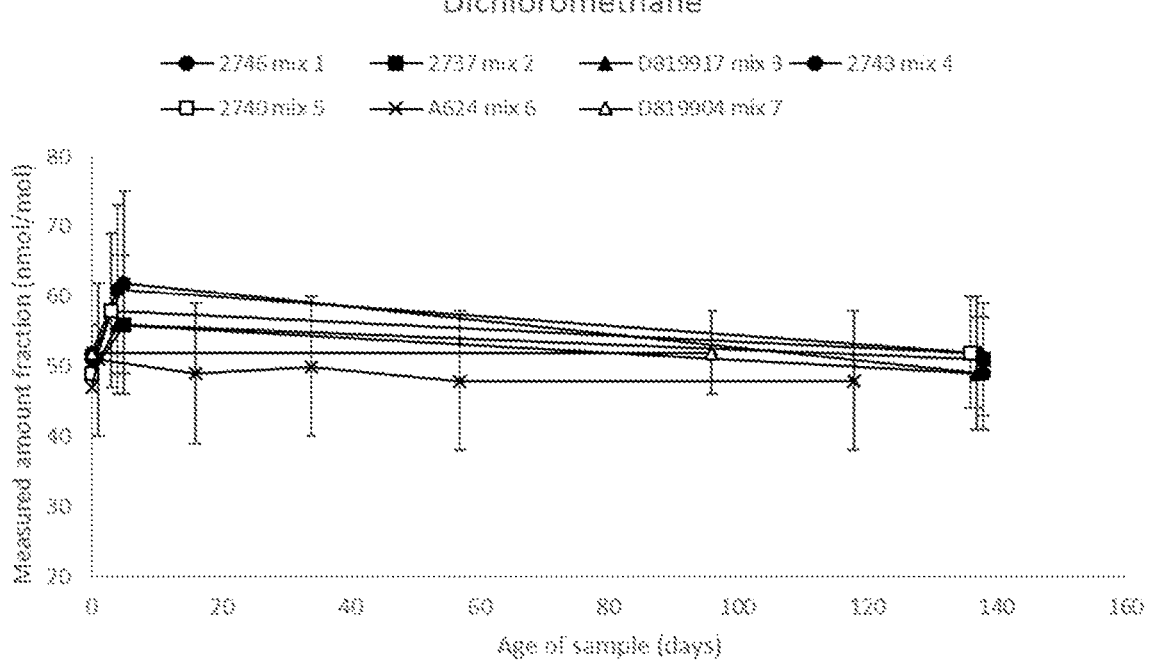
FIG. 6 shows the measured amount fraction of dichloromethane over time for the stability test samples. The value shown at age "0" days is the dichloromethane gravimetric amount fraction calculated from the preparation for each cylinder.

The amount fraction of dichloromethane in samples "Mix 1", "Mix 2", "Mix 3", "Mix 4", "Mix 5", "Mix 6" and "Mix 7" showed no initial loss within a 95% confidence level. The amount fraction of dichloromethane in these samples remained stable at a 95% confidence level for the duration of the stability test (137 days for "Mixes 1-5", 118 days for "Mix 6" and 96 days for "Mix 7"). This can be seen in FIG. 6.

4.7—Ethane (C$_2$H$_6$)

Figure 7:
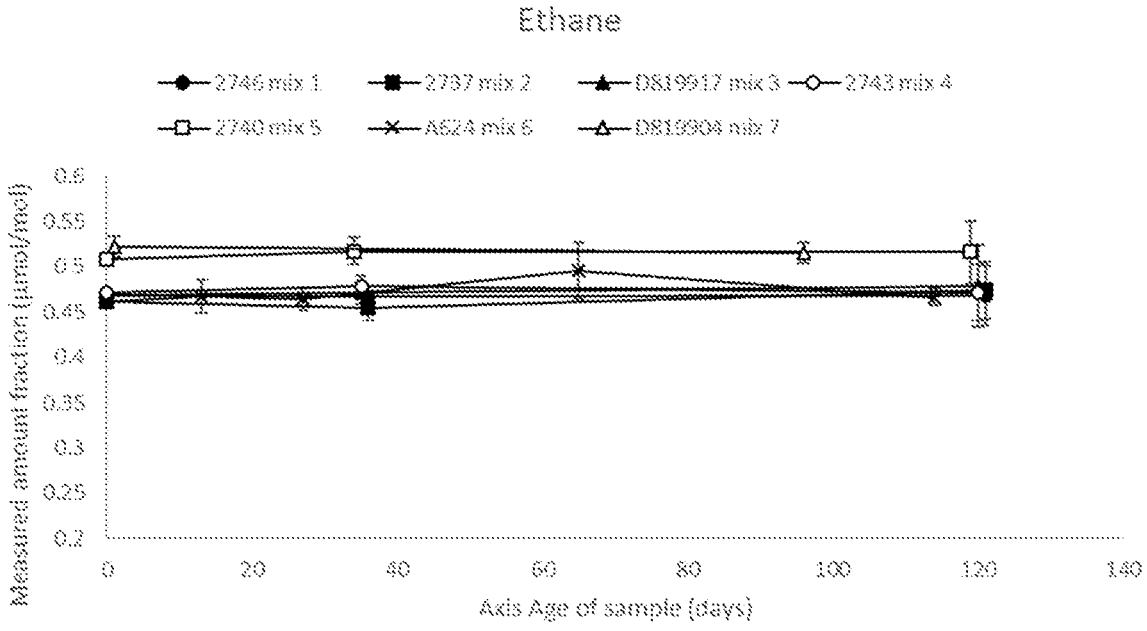
FIG. 7 shows the measured amount fraction of ethane over time for the stability test samples. The value shown at age "0" days is the ethane gravimetric amount fraction calculated from the preparation for each cylinder.

The amount fraction of dichloromethane in samples "Mix 1", "Mix 2", "Mix 3", "Mix 4", "Mix 5", "Mix 6" and "Mix 7" showed no initial loss within a 95% confidence level. The amount fraction of ethane in these samples remained stable at a 95% confidence level for the duration of the stability test (120 days for "Mixes 1-5", 114 days for "Mix 6" and 96 days for "Mix 7"). This can be seen in FIG. 7.

4.8—Formaldehyde (HCHO)

Formaldehyde in all samples showed rapid loss to below limit of detection, unless for "Mix 6" which kept measurable amount fractions of formaldehyde contaminant for the duration of the test (115 days). The main difference in composition between the mixtures was the increased amount fraction target of ammonia and the presence of measurable ammonia.

4.9—Formic Acid (HCOOH)

Figure 8:
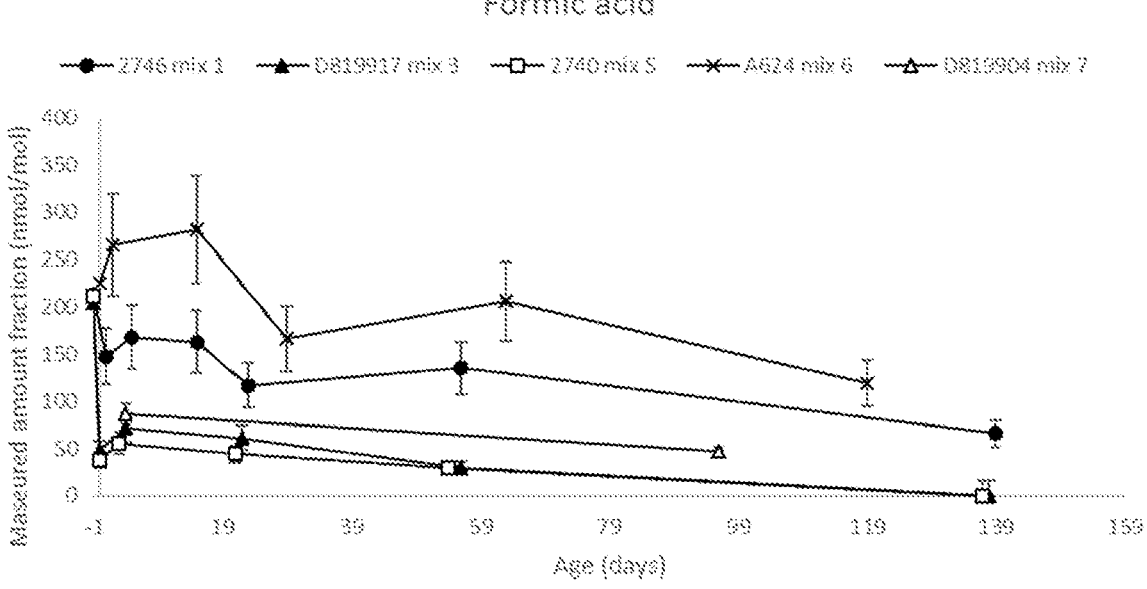
FIG. 8 shows the measured amount fraction of formic acid over time for the stability test samples. The value shown at age "−1" days is the formic acid gravimetric amount fraction calculated from the preparation for each cylinder.

The formic acid in samples "Mix 1", "Mix 3" and "Mix 5" showed an initial loss on preparation. "Mix 3" and "Mix 5" showed a greater initial loss than "Mix 1". After this initial loss the formic acid amount fraction in the samples remained stable within a 95% confidence level for 54-56 days depending on the preparation date of the sample. The measurement at 140 days show that the amount fractions in the samples had dropped in "Mix 1" by around 50% and in "Mix 3" and "Mix 5" to below limit of detection. "Mix 6" showed a similar stability period of around 60 days for formic acid before decay was seen at measurement time of 119 days. This can be seen in FIG. 8.

4.10—Helium (He)

Figure 9:
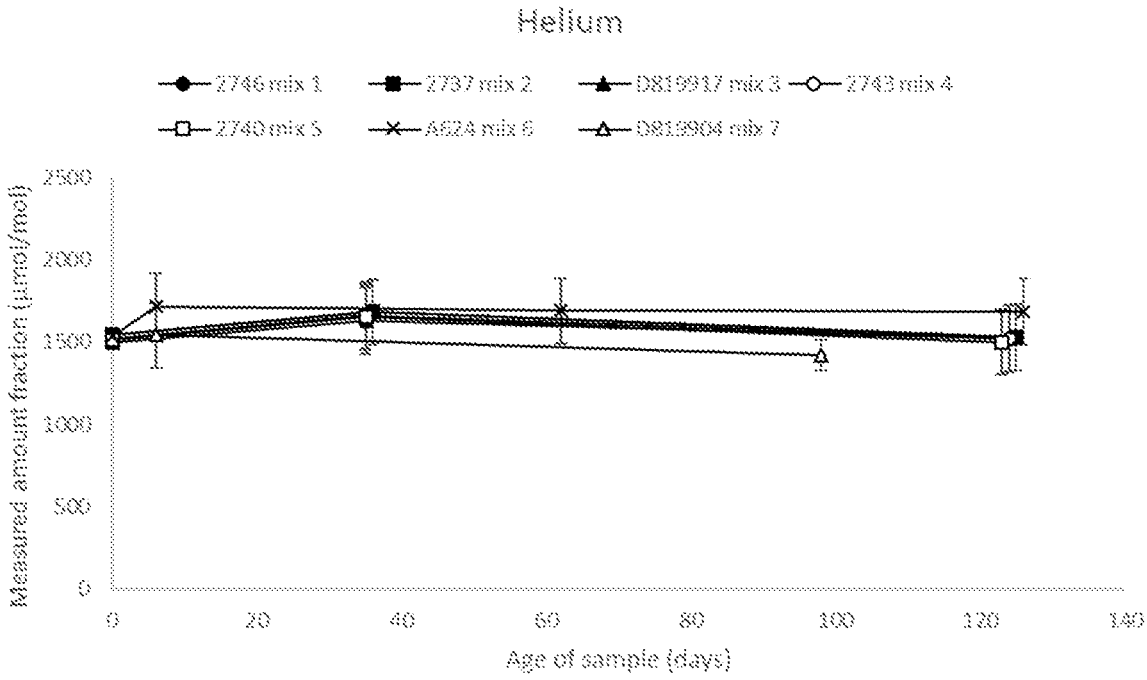
FIG. 9 shows the measured amount fraction of helium over time for the stability test samples. The value shown at age "0" days is the helium gravimetric amount fraction calculated from the preparation for each cylinder.

The amount fraction of helium in samples "Mix 1", "Mix 2", "Mix 3", "Mix 4", "Mix 5", "Mix 6" and "Mix 7" showed no initial loss within a 95% confidence level. The amount fraction of helium in these samples remained stable at a 95% confidence level for the duration of the stability test (123 days for "Mixes 1-5", 126 days for "Mix 6" and 98 days for "Mix 7"). This can be seen in FIG. 9.

4.11—Hydrogen Sulphide ($H_2S$)

Figure 10:
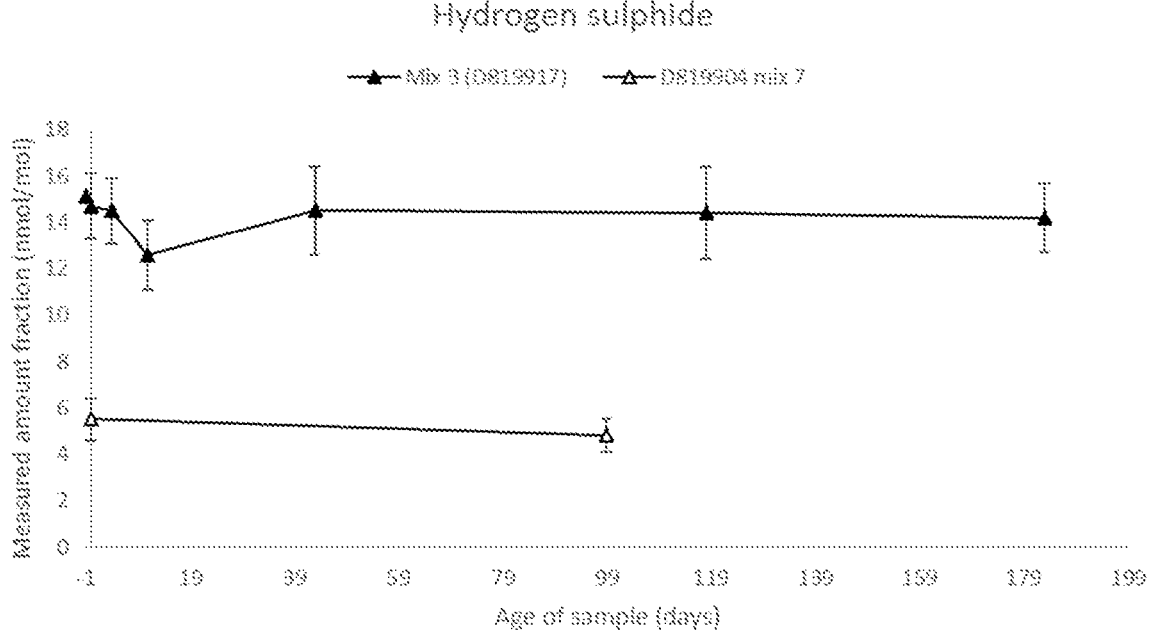
FIG. 10 shows the measured amount fraction of hydrogen sulphide over time for the stability test sample "Mix 3". The value shown at age "−1" days is the hydrogen sulphide gravimetric amount fraction calculated from the preparation for the cylinder "Mix 3".

The amount fraction of hydrogen sulphide in samples "Mix 1", "Mix 2", "Mix 4" and "Mix 6" showed initial loss of hydrogen sulphide to below limit of detection from initial measurement. The amount fraction of hydrogen sulphide in sample "Mix 3" and "Mix 7" showed no initial loss within a 95% confidence level. The amount fraction of hydrogen sulphide in "Mix 3" and "Mix 7" sample remained stable at a 95% confidence level for the duration of the stability test (183 days for "Mix 3" and 99 days for "Mix 7"). This can be seen in FIG. 10.

"Mix 2" and "Mix 4" had formic acid removed due to theorised interference between the hydrogen sulphide and formic acid in the samples. The hydrogen sulphide was below limit of detection in these two samples despite this. "Mix 3" had measurable formic acid within the sample but retained hydrogen sulphide without initial loss. "Mix 1", "Mix 2" and "Mix 4" were made in aluminium cylinders with SPECTRA-SEAL® internal treatment whereas "Mix 3" was made in an aluminium cylinder that had not undergone specialized passivation treatment. The internal treatment of the cylinder, therefore, has been shown to have a greater effect on the stability of hydrogen sulphide at near the ISO 14687 threshold limits.

4.12—Nitrogen ($N_2$)

Figure 11:
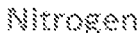
FIG. 11 shows the measured amount fraction of nitrogen over time for the stability test samples. The value shown at age "0" days is the nitrogen gravimetric amount fraction calculated from the preparation for each cylinder.
Figure 11:
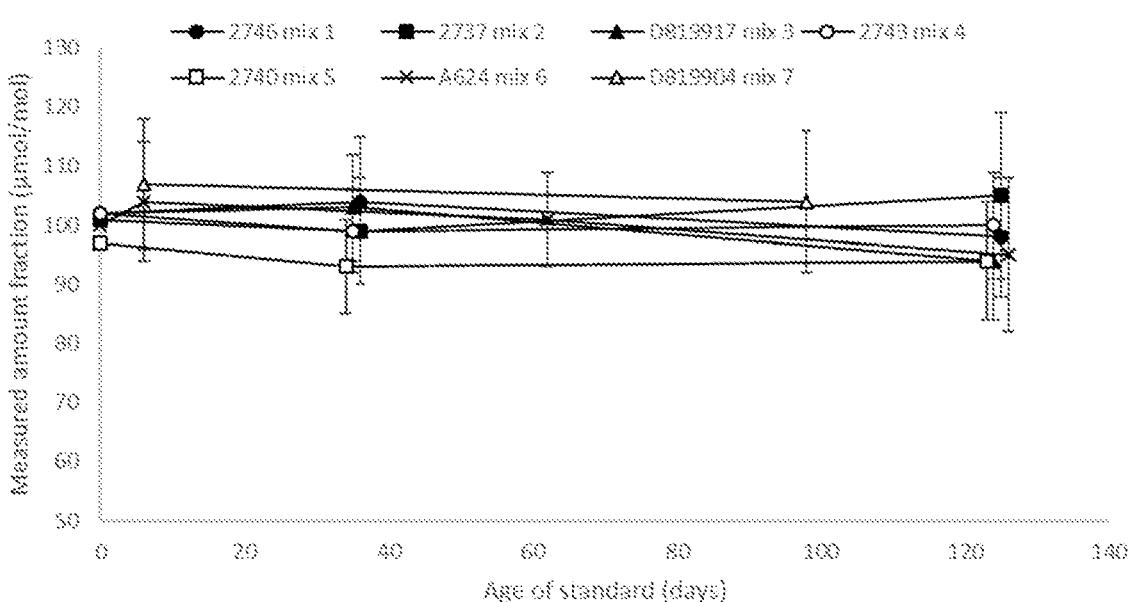

The amount fraction of nitrogen in samples "Mix 1", "Mix 2", "Mix 3", "Mix 4", "Mix 5", "Mix 6" and "Mix 7" showed no initial loss within a 95% confidence level. The amount fraction of nitrogen in these samples remained stable at a 95% confidence level for the duration of the stability test (123 days for "Mixes 1-5", 126 days for "Mix 6" and 98 days for "Mix 7"). This can be seen in FIG. 11.

4.13—Methane ($CH_4$)

Figure 12:
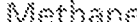
FIG. 12 shows the measured amount fraction of methane over time for the stability test samples. The value shown at age "0" days is the methane gravimetric amount fraction calculated from the preparation for each cylinder.
Figure 12:
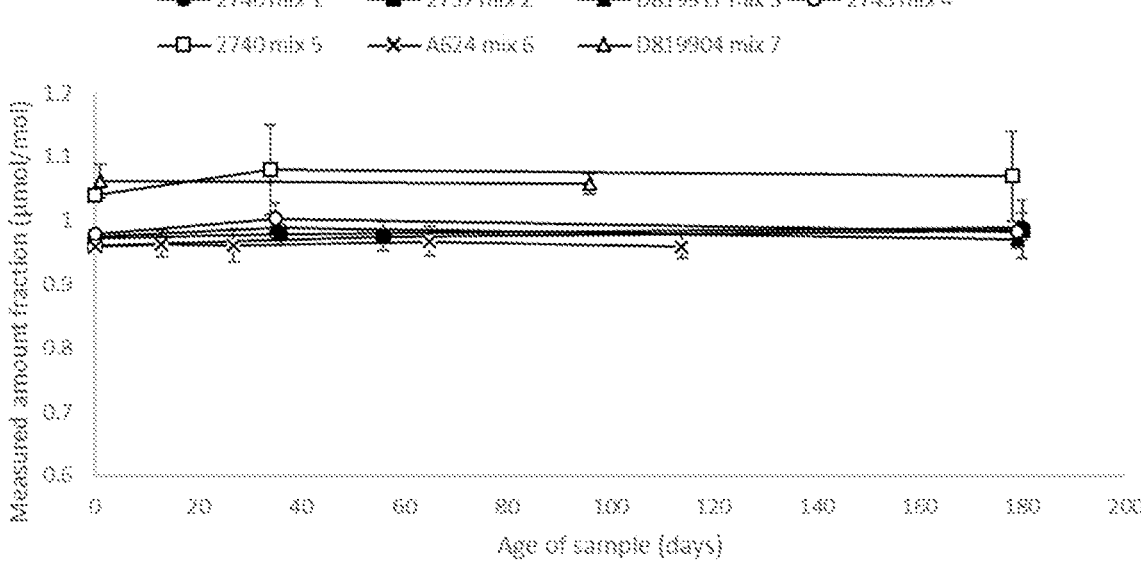

The amount fraction of methane in samples "Mix 1", "Mix 2", "Mix 3", "Mix 4", "Mix 5", "Mix 6" and "Mix 7" showed no initial loss within a 95% confidence level. The amount fraction of methane in these samples remained stable at a 95% confidence level for the duration of the stability test (180 days for "Mixes 1-5", 114 days for "Mix 6" and 96 days for "Mix 7"). This can be seen in FIG. 12.

4.14—Oxygen ($O_2$)

Figure 13:
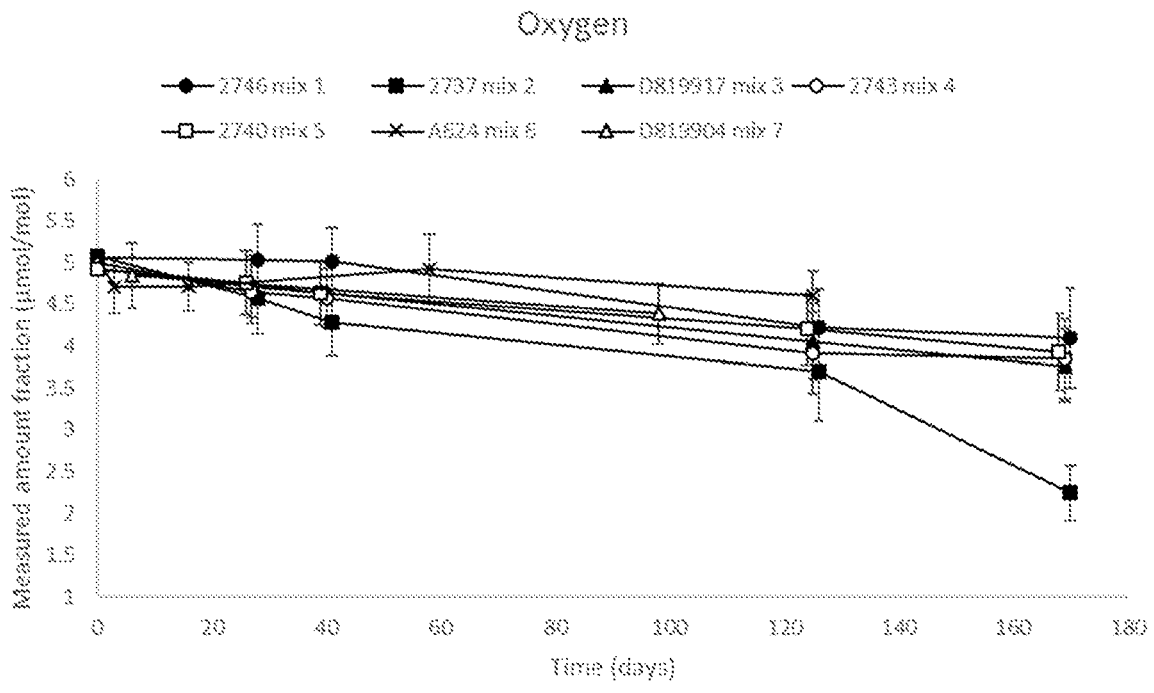
FIG. 13 shows the measured amount fraction of oxygen over time for the stability test samples. The value shown at age "0" days is the oxygen gravimetric amount fraction calculated from the preparation for each cylinder.

The amount fraction of oxygen in samples "Mix 1", "Mix 2", "Mix 3", "Mix 4" and "Mix 5" all showed decay of oxygen over the period of the stability test (180 days). All samples, excluding "Mix 2" and "Mix 4", measured stable oxygen within a 95% confidence level until time 40 days. The measurement at 125 days showed decay of all samples that was significant within a 95% confidence level. "Mix 6" showed stable $O_2$ for the duration of the stability test (125 days). This can be seen in FIG. 13.

"Mix 2" showed significantly greater decay of oxygen amount fraction over time than the other samples. This was accompanied by a significant increase in amount fraction of water in the sample (see section 4.15—below).

4.15—Water ($H_2O$)

Figure 14:
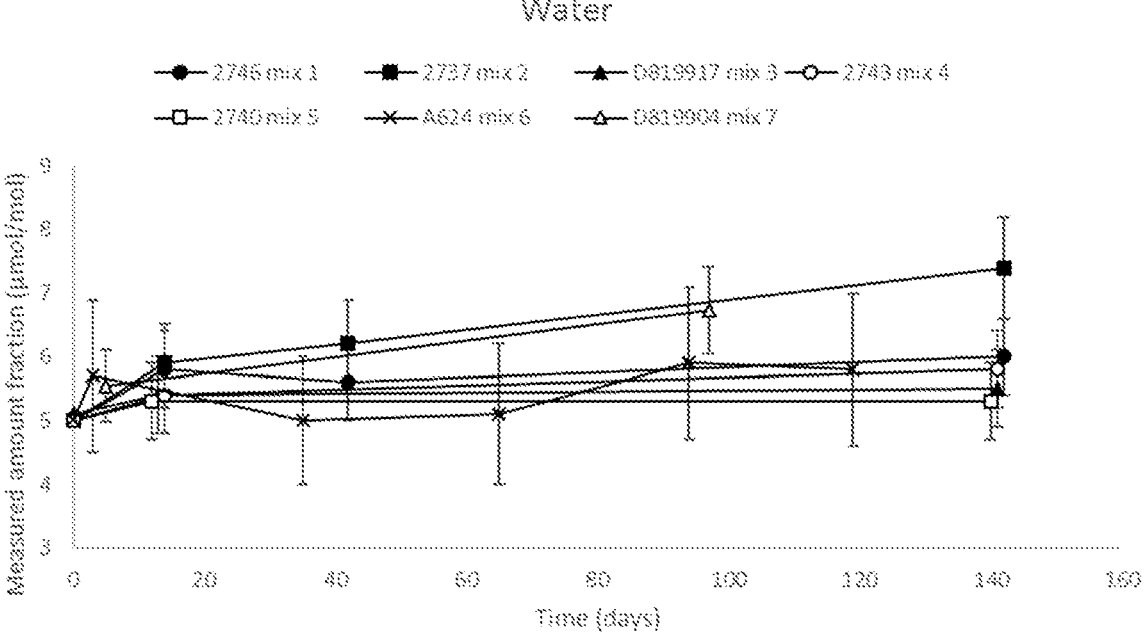
FIG. 14 shows the measured amount fraction of water over time for the stability test samples. The value shown at age "0" days is the water gravimetric amount fraction calculated from the preparation for each cylinder.

The amount fraction of water in "Mix 2" increased significantly over the period of the stability test. This corresponded with a significant loss of oxygen amount fraction in "Mix 2" as explained in section 4.15 above, and corresponds to the reaction of oxygen with the hydrogen matrix to form water. "Mix 6" showed stable water for the duration of the stability test (125 days). This can be seen in FIG. 14.

4.16—Summary of the Stability Results

TABLE 4b

| | Amount fraction (in μmol/mol) | | | | | | |
|---|---|---|---|---|---|---|---|
| Contaminants | "Mix 1" Silicon compound-based coating | "Mix 2" Silicon compound-based coating | "Mix 3" Aluminium | "Mix 4" Silicon compound-based coating | "Mix 5" Silicon compound-based coating | "Mix 6" Silicon compound-based coating | "Mix 7" Aluminium |
| Carbon monoxide (CO) | Stable | Stable | Stable | Stable | Stable | Stable | Stable |
| Carbon dioxide ($CO_2$) | Stable | Stable | Stable | Stable | Stable | Stable | Stable |
| Methane ($CH_4$) | Stable | Stable | Stable | Stable | Stable | Stable | Stable |
| Ethane ($C_2H_6$) | Stable | Stable | Stable | Stable | Stable | Stable | Stable |
| Nitrogen ($N_2$) | Stable | Stable | Stable | Stable | Stable | Stable | Stable |
| Argon (Ar) | Stable | Stable | Stable | Stable | Stable | Stable | Stable |
| Helium (He) | Stable | Stable | Stable | Stable | Stable | Stable | Stable |
| Ammonia ($NH_3$) | Initial loss then stable | Initial loss then stable | Initial loss then stable | Initial loss then stable | Initial loss then stable | Unstable | Initial loss then stable |
| Formic acid (HCOOH) | Initial loss then stable for 55 days | — | Initial loss then stable for 55 days | — | Initial loss then stable for 55 days | Stable for 55 days | Unstable |
| Formaldehyde (HCHO) | Unstable | — | Unstable | Unstable | Unstable | Initial loss then stable | Unstable |
| Hydrogen sulphide ($H_2S$) | Unstable | Unstable | Stable (0.005-0.015) | Unstable | — | Unstable | Stable (0.004-0.007) |

TABLE 4b-continued

| | Amount fraction (in μmol/mol) | | | | | | |
|---|---|---|---|---|---|---|---|
| Contaminants | "Mix 1" Silicon compound-based coating | "Mix 2" Silicon compound-based coating | "Mix 3" Aluminium | "Mix 4" Silicon compound-based coating | "Mix 5" Silicon compound-based coating | "Mix 6" Silicon compound-based coating | "Mix 7" Aluminium |
| Dichloromethane (CH$_2$Cl$_2$) | Stable | Stable | Stable | Stable | Stable | Stable | Stable |
| Water (H$_2$O) | Stability reliant on oxygen (O$_2$) | Unstable | Stability reliant on oxygen (O$_2$) | Stability reliant on oxygen (O$_2$) | Stability reliant on oxygen (O$_2$) | Stable | Stability reliant on oxygen (O$_2$) |
| Oxygen (O$_2$) | Stable for 40 days | Unstable | Stable for 40 days | Stable for 40 days | Stable for 40 days | Stable | Stable for 90 days |
| Carbonyl sulphide (OCS) | — | — | — | — | Stable | | — |

It follows from the above stability test that standard fuel samplings containing 13 of the 14 contaminants at close to the threshold limits listed in the ISO 14687 standard can be made as long as certain conditions are met. The contaminants that require special conditions are marked in the list below with an asterisk (*):

Argon
Ammonia*
Carbon dioxide
Carbon monoxide
Dichloromethane
Ethane
Formic acid*
Helium
Sulphur compound(s)*
Nitrogen
Methane
Oxygen*
Water*

The requirements for the asterisked components are the following: With ammonia, an increased target amount fraction is appropriately used when preparing the standard fuel mixture as there is an initial loss in preparation at the ISO 14687 threshold limits. An increased target amount fraction is appropriately used to overcome this initial loss. The value of 0.1 μmol/mol for ammonia is a certified measured value taking into account the initial loss of ammonia:

As with ammonia, formic acid also shows an initial loss during preparation. An increased target amount fraction needs be used to overcome this initial loss. The value of 0.2 μmol/mol for ammonia is a certified measured value taking into account the initial loss of formic acid.

For the sulphur compound(s), if hydrogen sulphide is desired over any other sulphur containing species, an untreated aluminium cylinder may appropriately be used. Carbonyl sulphide can be substituted if the standard fuel is being made in a cylinder treated internally with silicon-based compounds.

Oxygen and water are preferably used in connection with a pre-selected cylinder that has shown stability for oxygen amount fraction at close to the ISO 14687 threshold limits. This is due to cylinder-to-cylinder differences seen in the rate of decay for oxygen present in a hydrogen matrix. As oxygen may form water when reacting with the hydrogen matrix, the water stability is also linked to the oxygen stability if both are present in the standard fuel.

Formaldehyde cannot be prepared within a standard fuel that contains measurable ammonia because the latter interferes with formaldehyde at amount fractions close to the ISO 14687 limits. This poses a problem if both of these contaminants are present in the sample as one or more of the contaminants may be reduced to below the threshold limits. It follows however from the results obtained with "Mix 6" that a cylinder with a coating of silicon-based compounds can be used to prepare formaldehyde at ISO 14687 threshold limit amount fractions.

5—Stability Test in Hydrogen Standard Fuel Mixtures

Hydrogen standard fuel mixtures comprising the gas contaminants listed in Table 5 below have been prepared. Ticks (√) indicate that the contaminant is present. When the tick is marked with a [1], it denotes that the compound is present in the mixture but not at the ISO 14687:2019 standard threshold limits. When the tick is marked with a [2], it denotes that the compound is present in the mixture but requires overdosing during the preparation (because of initial losses). Cross marks (x) indicate that the contaminant is not present.

TABLE 5

| | Hydrogen fuel standard 1 | Hydrogen fuel standard 2 | Hydrogen fuel standard 3 | Hydrogen fuel standard 4 |
|---|---|---|---|---|
| Cylinder type | Surface-polished aluminium cylinder | Surface-polished aluminium cylinder | Aluminium cylinder with internal silicon compound-based film treatment | Aluminium cylinder with internal silicon compound-based film treatment |

TABLE 5-continued

|  | Hydrogen fuel standard 1 | Hydrogen fuel standard 2 | Hydrogen fuel standard 3 | Hydrogen fuel standard 4 |
|---|---|---|---|---|
| Cylinder preselection required | Yes | No | Yes | No |
| Minimum lifetime | 4 months (55 days for formic acid) | 4 months (55 days for formic acid) | 4 months (55 days for formic acid) | 4 months (55 days for formic acid) |
| Pressure | >20 bar | >20 bar | >20 bar | >20 bar |
| Contaminants |  |  |  |  |
| Carbon monoxide (CO) | ✓ | ✓ | ✓ | ✓ |
| Carbon dioxide (CO₂) | ✓ | ✓ | ✓ | ✓ |
| Methane (CH₄) | ✓ | ✓ | ✓ | ✓ |
| Ethane (C₂H₆) | ✓ | ✓ | ✓ | ✓ |
| Nitrogen (N₂) | ✓ | ✓ | ✓ | ✓ |
| Argon (Ar) | ✓ | ✓ | ✓ | ✓ |
| Helium (He) | ✓¹ | ✓ | ✓¹ | ✓ |
| Ammonia (NH₃) | x | ✓² | x | ✓² |
| Formic acid (HCOOH) | ✓² | ✓² | ✓² | ✓² |
| Formaldehyde (HCHO) | ✓² | x | ✓² | x |
| Hydrogen sulphide (H₂S) | ✓ | ✓ | x | x |
| Dichloromethane (CH₂Cl₂) | ✓ | ✓ | ✓ | ✓ |
| Water (H₂O) | ✓ | ✓ | ✓ | ✓ |
| Oxygen (O₂) | ✓ | x | ✓ | x |
| Carbonyl sulphide (OCS) | x | x | ✓ | ✓ |

Here, the surface-polished aluminium cylinder used in Hydrogen fuel standards 1 and 2 were LUXFER® aluminium cylinders with internal Nottingham finish, and the aluminium cylinders used in Hydrogen fuel standards 3 and 4 were aluminium cylinders subject to SPECTRA-SEAL® treatment.

The invention claimed is:

1. A hydrogen gas composition comprising the following gas contaminants in the following concentrations in a hydrogen gaseous matrix, expressed in μmol/mol with respect to the total number of moles of gas in the hydrogen gas composition as a whole:

sulphur compound(s): at least 0.002 μmol/mol and at most 0.20 μmol/mol, formaldehyde (HCHO): at least 0.05 μmol/mol at most 0.50 μmol/mol, formic acid (HCOOH): at least 0.05 μmol/mol and at most 0.50 μmol/mol, ammonia (NH₃): at least 0.050 μmol/mol and at most 0.50 μmol/mol, halogenated compound(s): at least 0.020 μmol/mol and at most 0.20 μmol/mol, the hydrogen gas composition comprising either ammonia (NH₃) or formaldehyde (HCHO) but not ammonia and formaldehyde simultaneously.

2. The hydrogen gas composition according to claim 1, additionally comprising the following further gas contaminants at the following concentrations in the hydrogen gaseous matrix, expressed in μmol/mol with respect to the total number of moles of gas in the hydrogen gas composition as a whole:

water (H₂O): at least 2.0 μmol/mol and at most 10 μmol/mol, oxygen (O₂): at least 2.0 μmol/mol and at most 10 μmol/mol.

3. The hydrogen gas composition according to claim 1, additionally comprising the following further gas contaminants at the following concentrations in the hydrogen gaseous matrix, expressed in μmol/mol with respect to the total number of moles of gas in the hydrogen gas composition as a whole:

hydrocarbon(s) except methane: at least 0.20 μmol/mol and at most 5.0 μmol/mol), methane (CH₄): at least 0.20 μmol/mol and at most 150 μmol/mol, helium (He): at least 150 μmol/mol and at most 2500 μmol/mol, nitrogen (N₂): at least 50 μmol/mol and at most 450 μmol/mol, argon (Ar): at least 50 μmol/mol and at most 450 μmol/mol, carbon dioxide (CO₂): at least 0.50 μmol/mol and at most 5.0 μmol/mol, carbon monoxide (CO): at least 0.10 μmol/mol and at most 0.5 μmol/mol.

4. A hydrogen gas composition according to claim 3, wherein the hydrocarbon(s) except methane comprise or consist of ethane (C₂H₆).

5. A hydrogen gas composition according to claim 1, wherein the sulphur compound(s) comprise or consist of hydrogen sulphide (H₂S) or carbonyl sulphide (OCS).

6. A hydrogen gas composition according to claim 1, wherein the halogenated compound(s) comprise or consist of dichloromethane (CH₂Cl₂).

7. A hydrogen gas composition according to claim 1, comprising ammonia (NH₃) but no formaldehyde (CH₂O).

8. A hydrogen gas composition according to claim 1, comprising formaldehyde (CH₂O) but no ammonia (NH₃).

9. A metal cylinder containing a hydrogen gas composition according to claim 1, under a pressure ranging from 20 to 200 bar.

10. A metal cylinder according to claim 9, which is an aluminium cylinder, coated aluminium cylinder or stainless steel cylinder.

11. An aluminium cylinder according to claim 10, wherein the inner surface of the aluminium cylinder is as obtained through a surface-polishing procedure, and hydrogen sulphide (H₂S) is present in the hydrogen gas composition.

12. An aluminium cylinder according to claim 10, wherein the inner surface of the aluminium cylinder is as obtained by a passivation process producing a film of silicon-based compound(s) on the aluminium substrate, and carbonyl sulphide (OCS) is present in the hydrogen gas composition.

13. A kit comprising:
  one metal cylinder according to claim 9 comprising a hydrogen gas composition and comprising ammonia, and
  one metal cylinder comprising a hydrogen gas composition and comprising formaldehyde.

14. A method for preparing a metal cylinder according to claim 9 comprising the steps of:
  (i) optionally pre-treating the inner surface of a metal, preferably aluminium, cylinder by pre-saturating the inside of the cylinder with ammonia ($NH_3$) and/or hydrogen sulphide ($H_2S$),
  (ii) introducing, into the cylinder obtained at the end of step (i), the gas contaminants providing the set of concentrations,
    ammonia ($NH_3$) not being introduced into the cylinder where formaldehyde (HCHO) is present, and vice versa, and
    with formaldehyde (HCHO) being introduced into the cylinder before formic acid (HCOOH).

15. A method according to claim 14, wherein the pre-saturation of step (i) is maintained during at least 48 hours, with ammonia ($NH_3$) and hydrogen sulphide ($H_2S$) concentrations higher than 10 μmol/mol, an aluminium cylinder being used and which is of the type obtained through a surface-polishing procedure.

16. A method according to claim 14, wherein the gas contaminants nitrogen ($N_2$), helium (He), argon (Ar), carbon monoxide (CO), carbon dioxide ($CO_2$), methane ($CH_4$), and ethane ($C_2H_6$), in their maximum individual concentrations, are introduced into the aluminium cylinder in the form of a pre-blended mixture during step (ii).

17. A method of using a hydrogen gas composition according to claim 1, comprising using the hydrogen gas composition as a calibration composition and/or quality control composition.

18. A method of using a hydrogen gas composition according to claim 17, comprising using the hydrogen gas composition as a calibration composition and/or quality control composition to analyse hydrogen fuel according to the ISO14687: 2019 standard.

19. A method of using a hydrogen gas composition according to claim 17, comprising using the hydrogen gas composition as a calibration composition and/or quality control composition to test hydrogen fuel in fuel cells.

20. A method of using a hydrogen gas composition according to claim 17, comprising using the hydrogen gas composition as a calibration composition and/or quality control composition for manufacturing hydrogen purifying devices, and preferably filters and hydrogen impurity sensors, in particular for fuel cell electric vehicles (FCEVs) or hydrogen refuelling stations (HRSs).

* * * * *